(12) United States Patent
Gardner et al.

(10) Patent No.: US 9,867,975 B2
(45) Date of Patent: Jan. 16, 2018

(54) ANTISEPTIC LINE CAP

(75) Inventors: Christopher E. Gardner, Manalapan, NJ (US); William Anderson, Cary, IL (US); Bruce Nanyung Lin, Somerset, NJ (US)

(73) Assignee: Excelsior Medical Corporation, San Clemente, CA (US)

( * ) Notice: Subject to any disclaimer, the term of this patent is extended or adjusted under 35 U.S.C. 154(b) by 329 days.

(21) Appl. No.: 13/113,777

(22) Filed: May 23, 2011

(65) Prior Publication Data

US 2012/0302997 A1    Nov. 29, 2012

(51) Int. Cl.
*A61M 39/20* (2006.01)
*A61M 39/16* (2006.01)

(52) U.S. Cl.
CPC ........ *A61M 39/20* (2013.01); *A61M 39/162* (2013.01); *A61M 39/165* (2013.01)

(58) Field of Classification Search
CPC ............... A61M 39/20; A61M 39/162; A61M 2039/1033; A61M 39/165; A61M 1/0052; A61M 1/0086; A61M 2039/0036; A61M 35/003; A61M 39/16; A61M 5/3202; A61M 2205/0205
USPC ........................................ 604/256, 533, 905
See application file for complete search history.

(56) References Cited

U.S. PATENT DOCUMENTS

| 877,946 | A | 2/1908 | Overton |
|---|---|---|---|
| 1,793,068 | A | 2/1931 | Dickinson |
| 2,098,340 | A | 11/1937 | Henahan |
| 2,436,297 | A | 2/1948 | Guarnaschelli |
| 3,270,743 | A | 9/1966 | Gingras |
| 3,301,392 | A | 1/1967 | Eddingfield |
| 3,882,858 | A | 5/1975 | Klemm |
| 3,977,401 | A | 8/1976 | Pike |
| 3,987,930 | A | 10/1976 | Fuson |
| 4,041,934 | A | 8/1977 | Genese |
| 4,095,810 | A | 6/1978 | Kulle |
| 4,243,035 | A | 1/1981 | Barrett |
| 4,280,632 | A | 7/1981 | Yuhara |
| 4,294,370 | A | 10/1981 | Toeppen |
| 4,317,446 | A | 3/1982 | Ambrosio et al. |

(Continued)

FOREIGN PATENT DOCUMENTS

| CA | 2148847 | 12/1995 |
|---|---|---|
| CA | 2169689 | 8/1996 |

(Continued)

OTHER PUBLICATIONS

Examination Report dated Jun. 6, 2011, issued by the Canadian Intellectual Property Office in connection with Canadian Patent Application No. 2,692,157 (2 pages).

(Continued)

*Primary Examiner* — Imani Hayman
*Assistant Examiner* — Brandy S Lee
(74) *Attorney, Agent, or Firm* — Knobbe Martens Olson & Bear, LLP

(57) ABSTRACT

An antiseptic cap assembly for use with a connector includes a cap with a base and an annular portion extending from the base. The annular portion defines a first chamber having an open end. The cap is made of an absorbent material. The antiseptic cap assembly also includes a cap holder having a generally cylindrical sidewall defining a second chamber sized to receive the cap.

36 Claims, 15 Drawing Sheets

(56) References Cited

U.S. PATENT DOCUMENTS

| | | | |
|---|---|---|---|
| 4,335,756 A | 6/1982 | Sharp et al. | |
| 4,384,589 A * | 5/1983 | Morris | 401/199 |
| 4,402,691 A | 9/1983 | Rosenthal et al. | |
| 4,417,890 A | 11/1983 | Dennehey et al. | |
| 4,427,126 A | 1/1984 | Ostrowsky | |
| 4,432,764 A | 2/1984 | Lopez | |
| 4,432,766 A | 2/1984 | Bellotti et al. | |
| 4,439,184 A | 3/1984 | Wheeler | |
| 4,440,207 A | 4/1984 | Genatempo et al. | |
| 4,444,310 A | 4/1984 | Odell | |
| 4,461,368 A | 7/1984 | Plourde | |
| 4,480,940 A * | 11/1984 | Woodruff | 401/206 |
| 4,507,111 A | 3/1985 | Gordon et al. | |
| 4,624,664 A | 11/1986 | Peluso et al. | |
| 4,666,057 A | 5/1987 | Come et al. | |
| 4,666,427 A | 5/1987 | Larsson et al. | |
| 4,671,306 A | 6/1987 | Spector | |
| 4,703,762 A | 11/1987 | Rathbone et al. | |
| 4,728,321 A | 3/1988 | Chen | |
| 4,747,502 A | 5/1988 | Luenser | |
| 4,752,983 A | 6/1988 | Grieshaber | |
| 4,778,447 A | 10/1988 | Velde et al. | |
| 4,799,926 A | 1/1989 | Haber | |
| 4,811,847 A | 3/1989 | Reif et al. | |
| 4,813,933 A | 3/1989 | Turner | |
| 4,927,019 A | 5/1990 | Haber et al. | |
| 4,957,637 A | 9/1990 | Cornell | |
| 4,983,161 A | 1/1991 | Dadson et al. | |
| 4,989,733 A | 2/1991 | Patry | |
| 4,991,629 A | 2/1991 | Ernesto et al. | |
| 5,143,104 A | 9/1992 | Iba et al. | |
| 5,190,534 A | 3/1993 | Kendell | |
| 5,205,821 A | 4/1993 | Kruger et al. | |
| 5,242,421 A | 9/1993 | Chan | |
| 5,242,425 A | 9/1993 | White et al. | |
| 5,246,011 A | 9/1993 | Calillouette | |
| D342,134 S | 12/1993 | Mongeon | |
| 5,352,410 A | 10/1994 | Hansen et al. | |
| 5,471,706 A | 12/1995 | Wallock et al. | |
| 5,536,258 A | 7/1996 | Folden | |
| 5,552,115 A * | 9/1996 | Malchesky | A01N 37/16 422/1 |
| 5,554,135 A | 9/1996 | Menyhay | |
| 5,580,530 A | 12/1996 | Kowatsch et al. | |
| 5,620,088 A | 4/1997 | Martin et al. | |
| 5,624,402 A | 4/1997 | Imbert | |
| 5,694,978 A | 12/1997 | Heilmann et al. | |
| 5,702,017 A | 12/1997 | Goncalves | |
| 5,722,537 A | 3/1998 | Sigler | |
| 5,792,120 A | 8/1998 | Menyhay | |
| 5,810,792 A | 9/1998 | Fangrow, Jr. et al. | |
| 5,820,604 A | 10/1998 | Fox et al. | |
| 5,827,244 A | 10/1998 | Boettger | |
| 5,941,857 A | 8/1999 | Nguyen et al. | |
| 5,954,957 A | 9/1999 | Chin-Loy et al. | |
| 5,971,972 A | 10/1999 | Rosenbaum | |
| D416,086 S | 11/1999 | Parris et al. | |
| 5,989,229 A | 11/1999 | Chiappetta | |
| 6,045,539 A | 4/2000 | Menyhay | |
| 6,116,468 A | 9/2000 | Nilson | |
| 6,117,114 A | 9/2000 | Paradis | |
| 6,126,640 A | 10/2000 | Tucker et al. | |
| 6,179,141 B1 | 1/2001 | Nakamura | |
| 6,202,870 B1 | 3/2001 | Pearce | |
| 6,206,134 B1 | 3/2001 | Stark et al. | |
| 6,227,391 B1 | 5/2001 | King | |
| 6,250,315 B1 | 6/2001 | Ernster | |
| 6,315,761 B1 | 11/2001 | Shcherbina et al. | |
| 6,394,983 B1 | 5/2002 | Mayoral et al. | |
| 6,550,493 B2 | 4/2003 | Williamson et al. | |
| 6,555,054 B1 * | 4/2003 | Kral | A61L 2/18 134/198 |
| 6,585,691 B1 | 7/2003 | Vitello | |
| 6,679,395 B1 | 1/2004 | Pfefferkorn et al. | |
| 6,679,870 B1 | 1/2004 | Finch et al. | |
| 6,685,694 B2 | 2/2004 | Finch et al. | |
| 6,716,396 B1 | 4/2004 | Anderson | |
| 6,827,766 B2 | 12/2004 | Carnes et al. | |
| 6,911,025 B2 | 6/2005 | Miyahar | |
| 6,943,035 B1 | 9/2005 | Davies et al. | |
| 7,056,308 B2 | 6/2006 | Utterberg | |
| 7,083,605 B2 | 8/2006 | Miyahara | |
| 7,282,186 B2 | 10/2007 | Lake, Jr. et al. | |
| 7,431,712 B2 | 10/2008 | Kim | |
| 7,452,349 B2 | 11/2008 | Miyahar | |
| 7,516,846 B2 | 4/2009 | Hansen | |
| 7,635,344 B2 | 12/2009 | Tennican et al. | |
| D607,325 S | 1/2010 | Rogers et al. | |
| 7,731,678 B2 | 6/2010 | Tennican et al. | |
| 7,731,679 B2 | 6/2010 | Tennican et al. | |
| 7,749,189 B2 | 7/2010 | Tennican et al. | |
| 7,753,891 B2 | 7/2010 | Tennican et al. | |
| 7,763,006 B2 | 7/2010 | Tennican | |
| 7,766,182 B2 | 8/2010 | Trent et al. | |
| 7,776,011 B2 | 8/2010 | Tennican et al. | |
| 7,780,794 B2 | 8/2010 | Rogers et al. | |
| 7,794,675 B2 | 9/2010 | Lynn | |
| 7,799,010 B2 | 9/2010 | Tennican | |
| 7,857,793 B2 | 12/2010 | Raulerson et al. | |
| 7,922,701 B2 | 4/2011 | Buchman | |
| 7,959,026 B2 | 6/2011 | Bertani | |
| 7,985,302 B2 | 7/2011 | Rogers et al. | |
| 7,993,309 B2 | 8/2011 | Schweikert | |
| 8,065,773 B2 | 11/2011 | Vaillancourt et al. | |
| 8,069,523 B2 | 12/2011 | Vaillancourt et al. | |
| 8,113,837 B2 | 2/2012 | Zegarelli | |
| 8,162,899 B2 | 4/2012 | Tennican | |
| 8,167,847 B2 | 5/2012 | Anderson et al. | |
| 8,206,514 B2 | 6/2012 | Rogers et al. | |
| 8,231,587 B2 | 7/2012 | Solomon et al. | |
| 8,231,602 B2 | 7/2012 | Anderson et al. | |
| 8,273,303 B2 | 9/2012 | Ferlic et al. | |
| 8,328,767 B2 | 12/2012 | Solomon et al. | |
| 8,336,152 B2 | 12/2012 | Kerr et al. | |
| 8,343,112 B2 | 1/2013 | Solomon et al. | |
| 8,361,408 B2 | 1/2013 | Lynn | |
| 8,372,045 B2 | 2/2013 | Needle et al. | |
| 8,419,713 B1 | 4/2013 | Solomon et al. | |
| 8,480,968 B2 | 7/2013 | Lynn | |
| 8,523,830 B2 | 9/2013 | Solomon et al. | |
| 8,523,831 B2 | 9/2013 | Solomon et al. | |
| 8,545,479 B2 | 10/2013 | Kitani et al. | |
| 8,641,681 B2 | 2/2014 | Solomon et al. | |
| 8,647,308 B2 | 2/2014 | Solomon et al. | |
| 8,647,326 B2 | 2/2014 | Solomon et al. | |
| 8,671,496 B2 | 3/2014 | Kerr et al. | |
| 8,740,864 B2 | 6/2014 | Hoang et al. | |
| 8,845,593 B2 | 9/2014 | Anderson et al. | |
| 8,968,268 B2 | 3/2015 | Anderson et al. | |
| 9,072,296 B2 | 7/2015 | Mills et al. | |
| 9,078,992 B2 | 7/2015 | Ziebol et al. | |
| 9,095,667 B2 | 8/2015 | Von Schuckmann | |
| 9,101,750 B2 | 8/2015 | Solomon et al. | |
| 9,114,915 B2 | 8/2015 | Solomon et al. | |
| 9,125,600 B2 | 9/2015 | Steube et al. | |
| 9,149,624 B2 | 10/2015 | Lewis | |
| 9,192,449 B2 | 11/2015 | Kerr et al. | |
| 9,242,084 B2 | 1/2016 | Solomon et al. | |
| 9,259,284 B2 | 2/2016 | Rogers et al. | |
| 9,259,535 B2 | 2/2016 | Anderson et al. | |
| 9,283,367 B2 | 3/2016 | Hoang et al. | |
| 9,283,368 B2 | 3/2016 | Hoang et al. | |
| 9,283,369 B2 | 3/2016 | Ma et al. | |
| 9,289,588 B2 | 3/2016 | Chen | |
| 9,302,049 B2 | 4/2016 | Tekeste | |
| 9,352,140 B2 | 5/2016 | Kerr et al. | |
| 9,352,141 B2 | 5/2016 | Wong | |
| 9,399,125 B2 | 7/2016 | Burkholz | |
| 9,408,971 B2 | 8/2016 | Carlyon | |
| 2002/0010438 A1 | 1/2002 | Finch et al. | |
| 2002/0193752 A1 | 12/2002 | Lynn | |
| 2003/0153865 A1 * | 8/2003 | Connell et al. | 604/28 |
| 2004/0034042 A1 | 2/2004 | Tsuji et al. | |
| 2004/0048542 A1 | 3/2004 | Thomaschefsky et al. | |

(56) References Cited

U.S. PATENT DOCUMENTS

| | | |
|---|---|---|
| 2004/0215148 A1 | 10/2004 | Hwang et al. |
| 2004/0258560 A1 | 12/2004 | Lake, Jr. et al. |
| 2005/0013836 A1 | 1/2005 | Raad |
| 2005/0065479 A1 | 3/2005 | Schiller et al. |
| 2005/0124970 A1 | 6/2005 | Kunin et al. |
| 2005/0147524 A1 | 7/2005 | Bousquet |
| 2005/0148930 A1 | 7/2005 | Hseih et al. |
| 2005/0203460 A1 | 9/2005 | Kim |
| 2005/0214185 A1 | 9/2005 | Castaneda |
| 2006/0030827 A1 | 2/2006 | Raulerson et al. |
| 2007/0112333 A1 | 5/2007 | Hoang et al. |
| 2007/0167910 A1 | 7/2007 | Tennican et al. |
| 2007/0187353 A1 | 8/2007 | Fox et al. |
| 2007/0249996 A1 | 10/2007 | Tennican et al. |
| 2007/0265578 A1 | 11/2007 | Tennican et al. |
| 2007/0282280 A1 | 12/2007 | Tennican |
| 2007/0287989 A1 | 12/2007 | Crawford et al. |
| 2008/0019889 A1* | 1/2008 | Rogers .................. A61B 19/34 422/292 |
| 2008/0027399 A1 | 1/2008 | Harding et al. |
| 2008/0033371 A1 | 2/2008 | Updegraff et al. |
| 2008/0039803 A1 | 2/2008 | Lynn |
| 2008/0058733 A1 | 3/2008 | Vogt et al. |
| 2008/0086091 A1 | 4/2008 | Anderson et al. |
| 2008/0093245 A1* | 4/2008 | Periasamy ............ A61M 5/007 206/438 |
| 2008/0095680 A1 | 4/2008 | Steffens et al. |
| 2008/0132880 A1 | 6/2008 | Buchman |
| 2008/0147047 A1 | 6/2008 | Davis et al. |
| 2008/0177250 A1 | 7/2008 | Howlett et al. |
| 2008/0235888 A1 | 10/2008 | Vaillancourt et al. |
| 2009/0008393 A1* | 1/2009 | Howlett et al. ................ 220/380 |
| 2009/0012426 A1 | 1/2009 | Tennican |
| 2009/0062766 A1 | 3/2009 | Howlett et al. |
| 2009/0093757 A1 | 4/2009 | Tennican |
| 2009/0099529 A1* | 4/2009 | Anderson et al. ............ 604/192 |
| 2009/0137969 A1 | 5/2009 | Colantonio et al. |
| 2009/0205151 A1 | 8/2009 | Fisher et al. |
| 2009/0205656 A1 | 8/2009 | Nishibayashi et al. |
| 2009/0259194 A1 | 10/2009 | Pinedjian et al. |
| 2010/0003067 A1 | 1/2010 | Shaw et al. |
| 2010/0047123 A1 | 2/2010 | Solomon et al. |
| 2010/0049170 A1 | 2/2010 | Solomon et al. |
| 2010/0050351 A1* | 3/2010 | Colantonio ............ A61L 2/18 15/104.93 |
| 2010/0059474 A1 | 3/2010 | Brandenburger et al. |
| 2010/0064456 A1 | 3/2010 | Ferlic |
| 2010/0152670 A1 | 6/2010 | Low |
| 2010/0160894 A1 | 6/2010 | Julian et al. |
| 2010/0172794 A1* | 7/2010 | Ferlic .................. A61L 2/238 422/28 |
| 2010/0242993 A1 | 9/2010 | Hoang et al. |
| 2010/0306938 A1 | 12/2010 | Rogers et al. |
| 2011/0030726 A1 | 2/2011 | Kerr et al. |
| 2011/0044850 A1 | 2/2011 | Solomon et al. |
| 2011/0046564 A1 | 2/2011 | Zhong |
| 2011/0064512 A1 | 3/2011 | Shaw et al. |
| 2011/0217212 A1* | 9/2011 | Solomon et al. .............. 422/292 |
| 2011/0232020 A1 | 9/2011 | Rogers et al. |
| 2011/0265825 A1 | 11/2011 | Rogers et al. |
| 2011/0277788 A1 | 11/2011 | Rogers et al. |
| 2011/0290799 A1 | 12/2011 | Anderson et al. |
| 2011/0311602 A1 | 12/2011 | Mills et al. |
| 2012/0031904 A1 | 2/2012 | Kuhn et al. |
| 2012/0039764 A1 | 2/2012 | Solomon et al. |
| 2012/0109073 A1 | 5/2012 | Anderson et al. |
| 2012/0157965 A1 | 6/2012 | Wotton et al. |
| 2012/0195807 A1 | 8/2012 | Ferlic |
| 2012/0216359 A1 | 8/2012 | Rogers et al. |
| 2012/0216360 A1 | 8/2012 | Rogers et al. |
| 2012/0283693 A1 | 11/2012 | Anderson et al. |
| 2012/0283696 A1 | 11/2012 | Cronenberg et al. |
| 2012/0296284 A1 | 11/2012 | Anderson et al. |
| 2012/0302970 A1 | 11/2012 | Tennican |
| 2012/0302997 A1 | 11/2012 | Gardner et al. |
| 2013/0030414 A1 | 1/2013 | Gardner et al. |
| 2013/0035667 A1 | 2/2013 | Anderson et al. |
| 2013/0072908 A1 | 3/2013 | Solomon et al. |
| 2013/0098398 A1 | 4/2013 | Kerr et al. |
| 2013/0123754 A1 | 5/2013 | Solomon et al. |
| 2013/0171030 A1 | 7/2013 | Ferlic et al. |
| 2013/0183635 A1 | 7/2013 | Wilhoit |
| 2013/0274686 A1 | 10/2013 | Ziebol et al. |
| 2014/0052074 A1 | 2/2014 | Tekeste |
| 2014/0101876 A1 | 4/2014 | Rogers et al. |
| 2014/0228809 A1 | 8/2014 | Wong |
| 2015/0018774 A1 | 1/2015 | Anderson et al. |
| 2015/0217106 A1 | 8/2015 | Banik et al. |
| 2015/0237854 A1 | 8/2015 | Mills et al. |
| 2015/0314119 A1 | 11/2015 | Anderson et al. |
| 2015/0314120 A1 | 11/2015 | Gardner et al. |
| 2015/0320926 A1 | 11/2015 | Fitzpatrick et al. |
| 2015/0374968 A1 | 12/2015 | Solomon et al. |
| 2016/0001058 A1 | 1/2016 | Ziebol et al. |
| 2016/0045629 A1 | 2/2016 | Gardner et al. |
| 2016/0067365 A1 | 3/2016 | Ma et al. |
| 2016/0067471 A1 | 3/2016 | Ingram et al. |
| 2016/0088995 A1 | 3/2016 | Ueda et al. |
| 2016/0089530 A1 | 3/2016 | Sathe |
| 2016/0101276 A1 | 4/2016 | Tekeste |
| 2016/0106969 A1 | 4/2016 | Neftel |
| 2016/0121097 A1 | 5/2016 | Steele |
| 2016/0144118 A1 | 5/2016 | Solomon et al. |
| 2016/0158520 A1 | 6/2016 | Ma et al. |
| 2016/0158521 A1 | 6/2016 | Hoang et al. |
| 2016/0158522 A1 | 6/2016 | Hoang et al. |
| 2016/0184527 A1 | 6/2016 | Tekeste |
| 2016/0213912 A1 | 7/2016 | Daneluzzi |
| 2016/0250420 A1 | 9/2016 | Maritan et al. |

FOREIGN PATENT DOCUMENTS

| | | |
|---|---|---|
| CA | 2583601 | 4/2006 |
| CA | 2626864 | 5/2007 |
| CA | 2651192 | 11/2007 |
| CA | 2615146 | 6/2008 |
| CN | 2402327 Y | 10/2000 |
| CN | 2815392 Y | 9/2006 |
| CN | 201150420 Y | 11/2008 |
| CN | 201519335 U | 7/2010 |
| DE | 29617133 | 1/1997 |
| EP | 0108785 | 5/1984 |
| EP | 0227219 | 7/1987 |
| EP | 0245872 | 11/1987 |
| EP | 0769265 | 4/1997 |
| EP | 1061000 | 12/2000 |
| EP | 1331020 | 7/2003 |
| EP | 1977714 | 10/2008 |
| EP | 2 444 117 | 4/2012 |
| FR | 2493149 A | 5/1982 |
| FR | 2782910 | 3/2000 |
| GB | 123221 | 2/1919 |
| GB | 2296182 | 6/1996 |
| GB | 2333097 | 7/1999 |
| GB | 2387772 | 10/2003 |
| JP | H04-99950 | 2/1992 |
| JP | 2002-291906 | 10/2002 |
| JP | 2006-182663 A | 7/2006 |
| RU | 2246321 | 2/2005 |
| WO | WO 83/03975 | 11/1983 |
| WO | WO 9812125 | 3/1998 |
| WO | WO 2004/035129 | 4/2004 |
| WO | WO 2004/112846 A2 | 12/2004 |
| WO | WO 2006/007690 | 1/2006 |
| WO | WO 2006/044236 | 4/2006 |
| WO | WO 2007/056773 | 5/2007 |
| WO | WO 2007/137056 A2 | 11/2007 |
| WO | WO 2008/086631 | 7/2008 |
| WO | WO 2008/089196 | 7/2008 |
| WO | WO 2008/100950 | 8/2008 |
| WO | WO 2008/140807 | 11/2008 |
| WO | WO 2009/002474 | 12/2008 |
| WO | WO 2009/117135 | 9/2009 |
| WO | WO 2009/123709 | 10/2009 |

(56) References Cited

FOREIGN PATENT DOCUMENTS

| WO | WO 2009/136957 | 11/2009 |
|---|---|---|
| WO | WO 2009/153224 | 12/2009 |
| WO | WO 2010/002757 | 1/2010 |
| WO | WO 2010/002808 | 1/2010 |
| WO | WO 2010/039171 | 4/2010 |
| WO | WO 2011/028722 | 3/2011 |
| WO | WO 2011/119021 | 9/2011 |
| WO | WO 2015/120336 | 8/2015 |
| WO | WO 2015/168677 | 11/2015 |

OTHER PUBLICATIONS

Examination Report dated Apr. 27, 2011, issued by the Canadian Intellectual Property Office in connection with Canadian Patent Application No. 2,692,157 (2 pages).
Examination Report dated Jan. 23, 2013, issued by the Canadian Intellectual Property Office in connection with Canadian Patent Application No. 2,692,157 (4 pages).
Notice of Allowance dated Oct. 2, 2013, issued by the Canadian Intellectual Property Office in connection with Canadian Patent Application No. 2,692,157 (1 page).
Office Action dated Oct. 2012, issued by the Intellectual Property Office of Colombia in connection with Colombian Patent Application No. 10.000.937 (9 pages).
Examination Report dated Jun. 13, 2011, issued by the Intellectual Property Office of New Zealand in connection with New Zealand Patent Application No. 582395 (2 pages).
Examination Report and Notice of Acceptance of Complete Specification dated Dec. 5, 2012, issued by the Intellectual Property Office of New Zealand in connection with New Zealand Patent Application No. 582395 (1 page).
Interview Summary dated Nov. 18, 2010, from U.S. Appl. No. 11/821,190 (4 pages).
Notice of Allowance dated Jul. 29, 2011, from U.S. Appl. No. 11/821,190 (6 pages).
Notification of First Office Action dated Aug. 3, 2011, issued by the State Intellectual Property Office of the People's Republic of China in connection with Chinese Patent Application No. 200880103854.5 (5 pages).
International Search Report of the International Searching Authority mailed Sep. 11, 2008, issued in connection with International Patent Application No. PCT/US08/07797 (2 pages).
Written Opinion of the International Searching Authority mailed Sep. 11, 2008, issued in connection with International Patent Appln. No. PCT/US08/07797 (3 pages).
Office Action dated Jun. 9, 2011 from U.S. Appl. No. 12/214,526 (7 pages).
Final Office Action dated Oct. 31, 2011 from U.S. Appl. No. 12/214,526 (8 pages).
Interview Summary dated Mar. 23, 2012 from U.S. Appl. No. 12/214,526 (3 pages).
Redacted version of letter from David A. Divine, Esq. of Lee & Hayes, dated May 27, 2011 (3 pages).
Redacted version of letter from David A. Divine, Esq. of Lee & Hayes, dated May 16, 2011 (3 pages).
Office Action dated Dec. 21, 2011 from U.S. Appl. No. 13/095,516 (27 pages).
Office Action dated Dec. 17, 2009 from U.S. Appl. No. 11/821,190 (10 pages).
Office Action dated Aug. 2, 2010 from U.S. Appl. No. 11/821,190 (14 pages).
Office Action dated Mar. 7, 2011 from U.S. Appl. No. 11/821,190 (16 pages).
Notice of Allowance dated Apr. 26, 2011 from U.S. Appl. No. 11/821,190 (9 pages).
Notification of Second Office Action dated Apr. 16, 2012, issued by the State Intellectual Property Office of the People's Republic of China in connection with Chinese Patent Application No. 200880103854.5 (4 pages).

Notification of Third Office Action dated Nov. 1, 2012, issued by the State Intellectual Property Office of the People's Republic of China in connection with Chinese Patent Application No. 200880103854.5 (4 pages).
Notice of Allowance dated May 16, 2012 from U.S. Appl. No. 13/095,516 (18 pages).
Non-final Office Action dated Dec. 14, 2012 from U.S. Appl. No. 13/456,853 (16 pages).
Final Office Action dated Aug. 27, 2013 from U.S. Appl. No. 13/456,853 (18 pages).
International Preliminary Report on Patentability dated Dec. 22, 2009, in connection with International Patent Application No. PCT/US08/07797 (4 pages).
Patent Examination Report No. 3 dated May 1, 2013, issued by the Intellectual Property Office of Australia in connection with Australian Patent Application No. 2008269133 (3 pages).
Examination Report dated Nov. 8, 2012, issued by the Intellectual Property Office of New Zealand in connection with New Zealand Patent Application No. 603404 (2 pages).
Non-final Office Action dated May 3, 2013 from U.S. Appl. No. 13/649,569 (15 pages).
Final Office Action dated Aug. 23, 2013 from U.S. Appl. No. 13/649,569 (19 pages).
International Search Report of the International Searching Authority mailed Oct. 26, 2012, issued in connection with International Patent Application No. PCT/US2012/037772 (5 pages).
Written Opinion of the International Searching Authority dated Oct. 26, 2012, issued in connection with International Patent Appln. No. PCT/US2012/037772 (7 pages).
International Preliminary Report on Patentability dated Nov. 26, 2013, issued in connection with International Patent Application No. PCT/US2012/037772 (1 page).
International Search Report of the International Searching Authority dated Nov. 19, 2012, issued in connection with International Patent Application No. PCT/US2012/038880 (5 pages).
Written Opinion of the International Searching Authority dated Nov. 19, 2012, issued in connection with International Patent Appln. No. PCT/US2012/038880 (8 pages).
International Preliminary Report on Patentability dated Nov. 20, 2013, issued in connection with International Patent Application No. PCT/US2012/038880 (1 page).
Memo concerning Official Action (known of at least as early as Feb. 25, 2013), issued in connection with Mexican Application No. MX/a/2010/000171 (2 pages).
Second Memo concerning Official Action (known of at least as early as Oct. 22, 2013), issued in connection with Mexican Application No. MX/a/2010/000171 (1 page).
Patent Examination Report dated Apr. 18, 2013, issued by the Intellectual Property Office of Australia in connection with Australian Patent Application No. 2012258435 (4 pages).
Innovation Patent Examination Report No. 1 dated Apr. 18, 2013, issued by the Intellectual Property Office of Australia in connection with Australian Patent Application No. 2013100345 (3 pages).
Notice of Acceptance dated Nov. 14, 2013, issued by the Intellectual Property Office of Australia in connection with Australian Patent Application No. 2008269133 (2 pages).
Menyhay, et al., "Disinfection of Needleless Catheter Connectors and Access Ports with Alcohol May Not Prevent Microbial Entry: The Promise of a Novel Antiseptic-Barrier Cap" Infection Control Hospital and Epidemiology, vol. 27, No. 1 (Jan. 2006) (5 pages).
International Standard, "Conical fittings with 6% (Luer) Taper for Syringes, Needles and Certain Other Medical Equipment- Part 2: Lock Fittings" Ref. No. ISO 594-2: 1998. International Organization for Standardization (Sep. 1, 1998) 2nd ed. (16 pages).
Examination Report dated Nov. 8, 2012, issued by the Intellectual Property Office of New Zealand in connection with New Zealand Patent Application No. 582395 (2 pages).
Patent Examination Report No. 1 dated Aug. 27, 2012, issued by the Intellectual Property Office of Australia in connection with Australian Patent Application No. 2008269133 (4 pages).
Patent Examination Report No. 2 dated Jan. 9, 2013, issued by the Intellectual Property Office of Australia in connection with Australian Patent Application No. 2008269133 (3 pages).

(56) References Cited

OTHER PUBLICATIONS

Non-final Office Action dated Mar. 27, 2014 from U.S. Appl. No. 13/456,853 (14 pages).
Non-final Office Action dated Apr. 14, 2014 from U.S. Appl. No. 13/649,569 (27 pages).
Non-final Office Action dated Feb. 8, 2013 from U.S. Appl. No. 13/473,057 (20 pages).
Final Office Action dated Dec. 3, 2013 from U.S. Appl. No. 13/473,057 (19 pages).
First Examination Report dated Apr. 8, 2014, issued by the Intellectual Property Office of New Zealand in connection with New Zealand Patent Application No. 623139 (1 page).
First Examination Report dated Apr. 9, 2014, issued by the Intellectual Property Office of New Zealand in connection with New Zealand Patent Application No. 623141 (1 page).
First Office Action dated May 4, 2014, along with English translation, issued by the State Intellectual Property Office of the People's Republic of China in connection with Chinese Patent Application No. 201310087320.0 (20 pages).
International Search Report of the International Searching Authority mailed Feb. 14, 2013, issued in connection with International Patent Application No. PCT/US2012/062078 (3 pages).
Written Opinion of the International Searching Authority mailed Feb. 14, 2013, issued in connection with International Patent Appln. No. PCT/US2012/062078 (3 pages).
International Preliminary Report on Patentability mailed May 6, 2014, issued in connection with International Patent Application No. PCT/US2012/062078 (4 pages).
Notice of Allowance dated Dec. 3, 2014, from U.S. Appl. No. 13/456,853 (9 pages).
International Search Report of the International Searching Authority mailed Jul. 28, 2014, issued in connection with International Patent Application No. PCT/US2014/23140 (3 pages).
Written Opinion of the International Searching Authority mailed Jul. 28, 2014, issued in connection with International Patent Appln. No. PCT/US2014/23140 (6 pages).
First Examination Report dated Dec. 5, 2014, issued by the Intellectual Property Office of New Zealand in connection with New Zealand Patent Application No. 624449 (2 pages).
Supplemental Expert Report of Charles Clemens, dated Aug. 15, 2014 (22 pages).
Non-Final Office Action dated Jan. 29, 2015 from U.S. Appl. No. 13/547,650 (9 pages).
Non-final Office Action dated Jan. 29, 2015 from U.S. Appl. No. 13/649,569 (14 pages).
Office Action dated Nov. 21, 2014, issued by the Intellectual Property Office of Japan in connection with Japanese patent Application No. 2013-162527 (2 pages).
Non-final Office Action dated Feb. 11, 2015 from U.S. Appl. No. 13/560,499 (9 pages).
Non-Final Office Action dated Apr. 8, 2015 from U.S. Appl. No. 13/288,529 (12 pages).
Final Office Action dated Mar. 31, 2015 from Japanese Application No. 2010-163450 (3 pages).
Non-Final Office Action dated Jun. 24, 2015 from U.S. Appl. No. 13/476,772 (10 pages).
Non-Final Office Action dated Jul. 1, 2015 from U.S. Appl. No. 13/968,151 (8 pages).
Non-Final Office Action dated Jul. 31, 2015 from U.S. Appl. No. 13/803,289 (7 pages).
Office Action dated Jul. 2015, issued by the Intellectual Property Office of Colombia in conenction with Colombian Patent Application No. 14-094.083 (13 pages).
Examination Report dated Apr. 30, 2015, issued by the Canadian Intellectual Property Office in connection with Canadian Patent Application No. 2,846,145 (3 pages).
Patent Examination Report dated May 19, 2015, issued by the Intellectual Property Office of Australia in connection with Australian Patent Application No. 2013224680 (2 pages).
Photographs of the Baxter Minicap (Sep. 1, 1998) (4 pages).
Baxter, "Peritoneal Dialysis Patient Connectology," Product Descriptions in 1 page, downloaded Jul. 1, 2011.
Catheter Connections, "Introducing DualCap," Product Brochure in 1 page, Copyright 2011.
Hyprotek, "Port Protek," Product Brochure in 1 page, downloaded Sep. 19, 2011 from http://www.hyprotek.com/products.html.

* cited by examiner

ANTISEPTIC LINE CAP

FIELD OF THE INVENTION

The present invention relates to an antiseptic cap, and more particularly, to an antiseptic line cap for a medical connector.

BACKGROUND OF THE INVENTION

Catheters are widely used to treat patients requiring a variety of medical procedures. Catheters can either be acute, or temporary, for short-term use or chronic for long-term treatment. Catheters are commonly caped into central veins (such as the vena cava) from peripheral vein sites to provide access to a patient's vascular system.

In a IV dispensing system, one end of a luer connector includes a fluid line which is connected to a fluid source, such as a IV bag filled with fluid. The other end of the male luer connector may be removably attached to one end of a female needleless luer connector. The other end of the female needleless luer connector may be attached to a catheter that has been caped into a patient.

When the male luer connector and the female needleless luer connector are attached to each other, fluid from the IV bag can flow into the patient. These connectors are often separated from each other at various times, for example, when a patient needs to use the bathroom. When the connectors are disengaged from each other, the connectors are exposed and are prone to contamination. Current procedures to reduce contamination of the connectors involve swabbing the connectors with a disinfection. These procedures are prone to human error and are often not implemented. Furthermore, when a male luer connector is disengaged from a female needleless connector, there is no standard manner in which to store the male luer connector, and protect it, until it is reattached to the female connector.

SUMMARY OF THE INVENTION

The present invention relates to an antiseptic cap for use with a connector. The antiseptic cap includes a cap having a base and an annular portion extending from the base. The annular portion defines a chamber having an open end. The cap could be made of an absorbent material.

An antiseptic cap assembly for use with a connector includes a cap having a base and an annular portion extending from the base. The annular portion defines a first chamber having an open end. The cap is made of a porous plastic material, and at least a portion of the cap includes an antiseptic fluid. The antiseptic cap assembly also includes a cap holder having a generally cylindrical sidewall defining a second chamber sized to receive the cap.

In another aspect, an antiseptic cap assembly for use with a connector includes a cap having a base and an annular portion extending from the base. The annular portion defines a first chamber having an open end. At least a portion of the cap is coated with an antiseptic material, and configured to release the antiseptic material when compressed.

BRIEF DESCRIPTION OF THE DRAWINGS

For a more complete understanding of the present invention, reference is made to the following Detailed Description of the Invention, considered in conjunction with the accompanying drawings, in which.

DETAILED DESCRIPTION OF THE INVENTION

The present invention relates to an antiseptic cap assembly that engages a male end of a luer connector. It should be understood, however, that the teachings herein can be used with other types of medical connectors.

Figure 1:
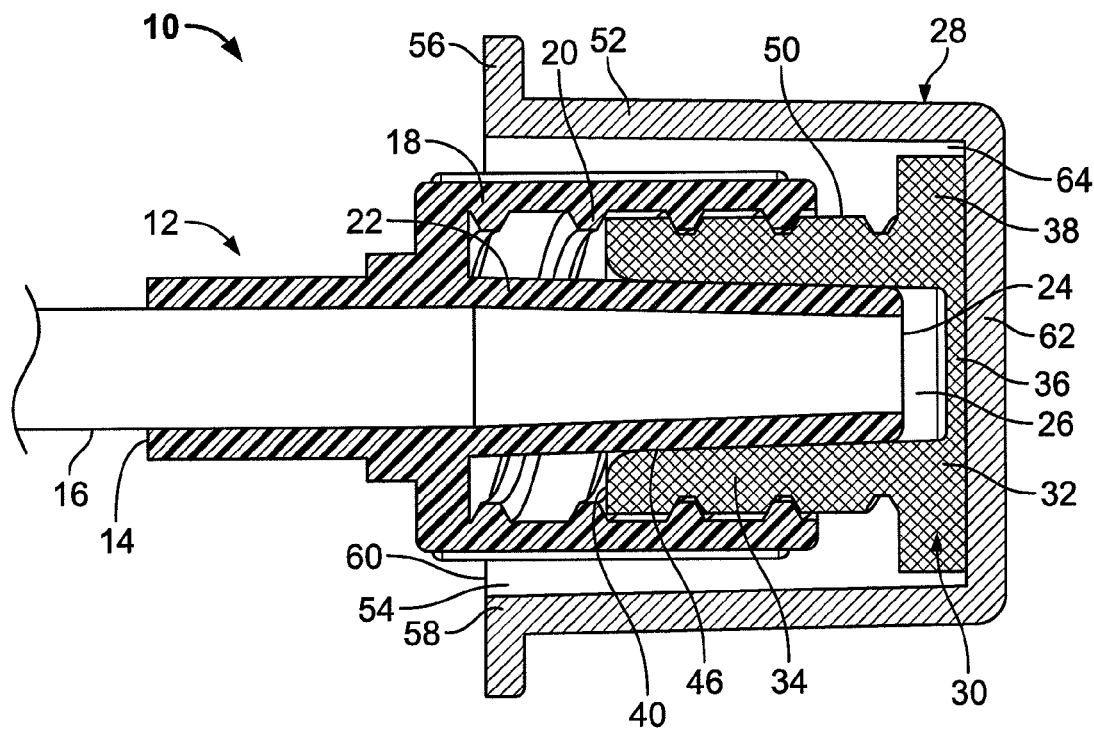
FIG. 1 is a cross-sectional view of an antiseptic cap assembly engaged to a luer connector according to the present invention.

FIG. 1 is a cross-sectional view of an antiseptic cap assembly 10 engaged to a luer connector 12. A proximal end 14 of the luer connector 12 is attached to a fluid line 16 which is connected to a fluid source (not shown), such as a IV bag filled with fluid. The luer connector 12 includes an annular threaded portion 18 with internal threads 20 and a frustoconical male luer 22 positioned for insertion into a female luer connector (not shown). The male luer 22 includes a tip 26 having an opening 24 in fluid communication with the fluid line 16. The male luer 22 is arranged substantially concentrically within the threaded portion 18. As a result of their generally coaxial arrangement, the male luer 22 and the threaded portion 18 cooperate to form an annular space therebetween.

The antiseptic cap assembly 10 includes a cap holder 28 and a cap 30 sized to be positioned within the cap holder 28. The cap 30 includes a base 32 and an annular threaded portion 34 extending from the base 32. The base 32 could include a substantially flat surface 36 and an outer flange 38.

Figure 3:
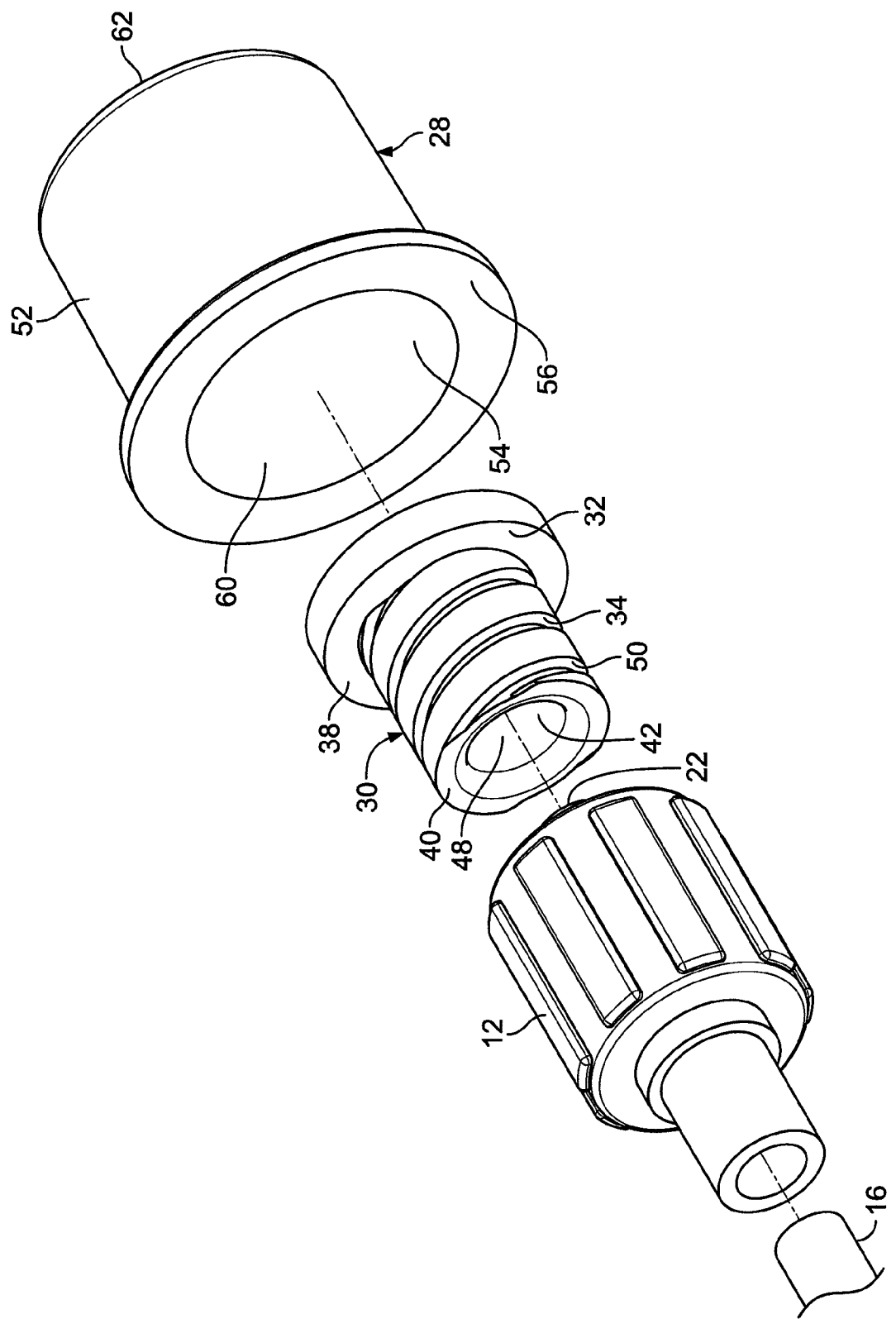
FIG. 3 is an exploded perspective view showing the antiseptic cap assembly of FIG. 1 and a luer connector.

The threaded portion 34 of the cap 30 includes a rim 40 that defines an open end 42 (see FIG. 3). The base 32 closes the opposite end of the threaded portion 34. The threaded portion 34 could be formed with a tapered inner surface 46 that compliments the male luer 22 of the luer connector 12. In particular, the tapered inner surface 46 narrows from the rim 40 toward the base 32. The threaded portion 34 defines a chamber 48 (see FIG. 3) sized to receive the male luer 22. The threaded portion 34 includes external threads 50 for engaging the threads 20 of the luer connector 12. The external threads 50 and the threads 20 of the luer connector 12 cooperate with each other so as to allow the cap 30 to be securely threadedly connected to the luer connector 12 and also to allow relative movement between the cap 30 and the luer connector 12, as the cap 30 is rotated relative to the luer connector 12. The external threads 50 extend between the base 32 and the rim 40.

The configuration of the cap 30 is shown in perspective in FIG. 3. It should be noted that this configuration is exemplary. For example, the cap 30 could be configured without threads and sized to engage the luer connector 12 with a push-on friction fit, as will be described hereinafter.

The cap 30 could be made from an absorbent material. The cap 30 could be made from porous plastic, for example, a medical grade sintered porous plastic material which is available from Porex. Corporation, based in Fairburn, Ga. Other suitable manufacturers of the porous plastic material include Filtrona, Genpore, and Thermopore. It is desirable that the material can absorb and retain a fluid such as an antiseptic fluid. It is also desirable that the material is sufficiently rigid to maintain its structure. It is also desirable that the material is compressible and that the absorbed fluid is released on compression. The porous plastic material could be made of any suitable polymer, such as polyethylene, polypropylene, nylon, etc.

The use of the porous plastic material is only exemplary. It will be understood that the cap 30 could be made from any other suitable material, such as bonded fiber, cotton, silicone, urethane, polyester, cellulose, etc. The material could be natural or synthetic.

The threaded portion 34 of the cap 30 could be coated or impregnated with an antiseptic fluid, an anticoagulant fluid, and/or an antimicrobial fluid. An example of a suitable antiseptic fluid is isopropyl alcohol. The concentration of the isopropyl alcohol could vary, and is preferably 70% v/v. The concentration of alcohol could be in a range from 20% to 100%. It will be understand that other materials could be used, such as other alcohols, including ethanol, propanol, and/or butanol, or iodine, hydrogen peroxide, chlorhexidine gluconate, chlorhexidine acetate, etc. The antiseptic, anticoagulant, and/or antimicrobial agent could be in liquid or solid form.

The cap holder 28 includes a cylindrically shaped sidewall 52 that defines a chamber 54 sized to receive the cap 30 and accommodate the male luer 22. The cap holder 28 could include an outer flange 56 that protrudes radially outwardly from a distal end 58 of the sidewall 52. The outer flange 56 defines an open end 60. The cap holder 28 could include a substantially flat surface 62 that defines the opposite, closed end. The cap holder 28 could be made from a thermoplastic elastomer, such as the thermoplastic elastomer sold by ExxonMobil under the trademark SANTOPRENE, or any other suitable material. The cap holder 28 could be made from a more rigid material, such as a high-density polyethylene. The cap holder 28 and the cap 30 could be bonded to each other, or attached to each other by any suitable method, such as by adhesive or by molding.

When the cap 30 is attached to the cap holder 28, a gap 64 exists between the flange 38 of the cap 30 and the cap holder 28, and between the threaded portion 34 of the cap 30 and the cap holder 28. Also, the cap 30 is attached to the cap holder 28 such that the cap 30 rotates conjointly with the cap holder 28.

Figure 2:
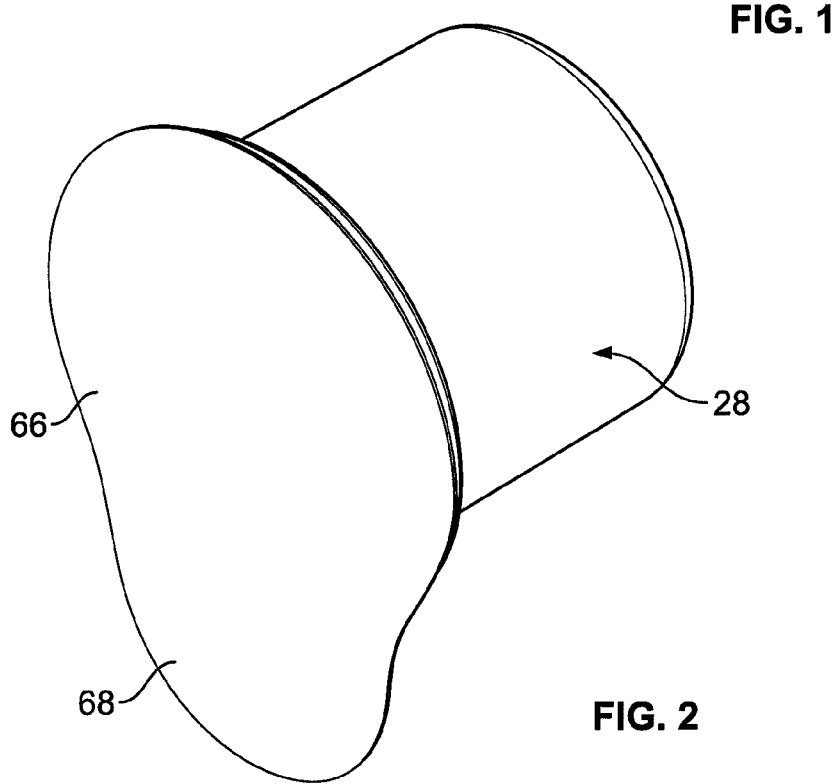
FIG. 2 is a perspective view of a sealed antiseptic cap assembly.

As shown in FIG. 2, the cap holder 28 could be sealed with a material, such as a film 66, a foil material or lid stock material, which can be attached to the flange 56 by any suitable method such as by adhesive or by conductive or inductive heat sealing techniques. A pull tab 68 could be provided to facilitate removal of the film 66 to provide access to the antiseptic cap 10.

Generally, the cap 30 may be hydrophobic. However, because the hydrophobic material could serve to inhibit or minimize an antiseptic fluid, such as isopropyl alcohol, from passing through the cap 30, it may be desirable to make at least a portion of the cap 30 hydrophilic. For example, it may be desirable to treat at least a portion of the cap 30 with a hydrophilic surfactant. In this manner, the hydrophilic portion could allow the alcohol to pass therethrough, whereas the hydrophobic portion could serve to inhibit or minimize an antiseptic fluid, such as isopropyl alcohol, from passing therethrough. In one embodiment, the threaded portion 34 could be treated with a hydrophilic surfactant whereas the base 32 could remain hydrophobic, so as to be resistant to an antiseptic fluid, such as alcohol. The hydrophobic section could also act as a plug to prevent IV fluid from leaking through the tubing to go past the cap 30.

Figure 4:
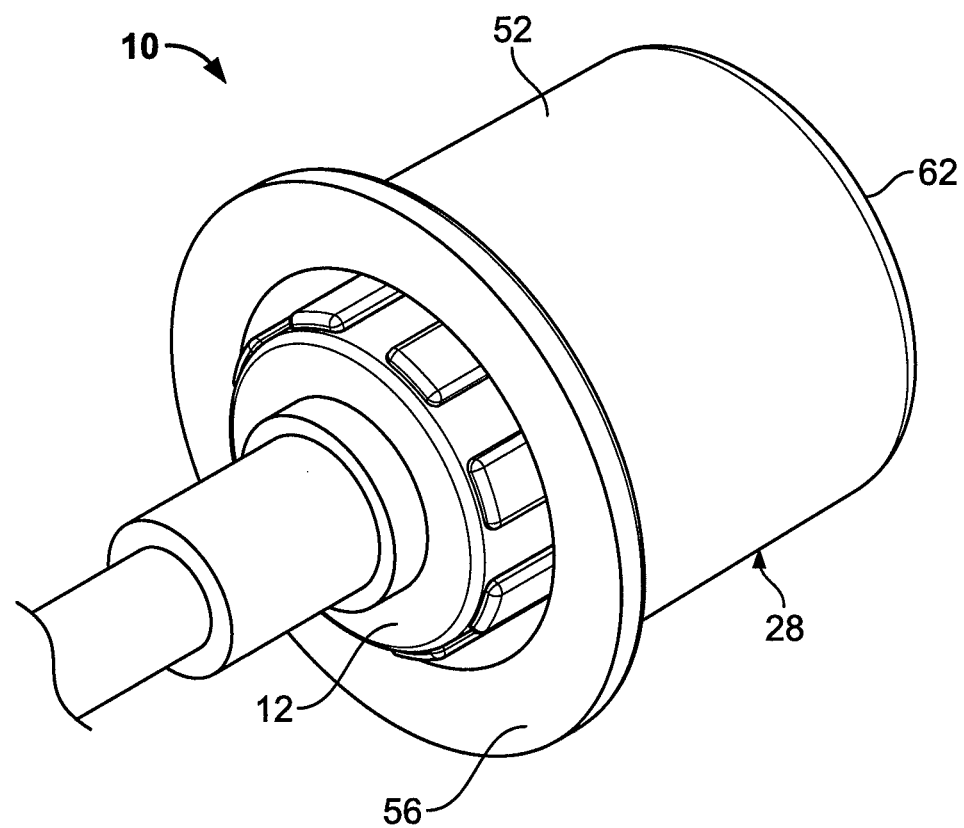
FIG. 4 is a perspective view of the antiseptic cap assembly of FIG. 1 engaged to a luer connector.

Referring to FIG. 1, the antiseptic cap assembly 10 is shown attached to the luer connector 12 such that the threaded portion 34 of the cap 30 mates with the threads 20 of the luer connector 12 and the base 32 is positioned adjacent the opening 24 of the male luer 22. Also, in this position, the inner surface 46 of the threaded portion 34 is adjacent the male luer 22 and the male luer 22 compresses the cap 30 to release at least a portion of the antiseptic fluid to disinfect the luer connector 12. The antiseptic cap assembly 10 can be allowed to remain attached to the luer connector 12 for any suitable period of time. When the antiseptic cap assembly 10 is attached to the luer connector 12, as shown in the perspective view of FIG. 4, the luer connector 12 is exposed to the antiseptic fluid.

The cap holder 28 could be configured to remain on the cap 30 after the antiseptic cap assembly 10 engages the luer connector 12. Alternatively, the cap holder 28 could be configured to be removably attached to the cap 30. For example, the cap holder 28 could be removed from the cap 30 after the antiseptic cap assembly 10 engages the luer connector 12.

Figure 5:
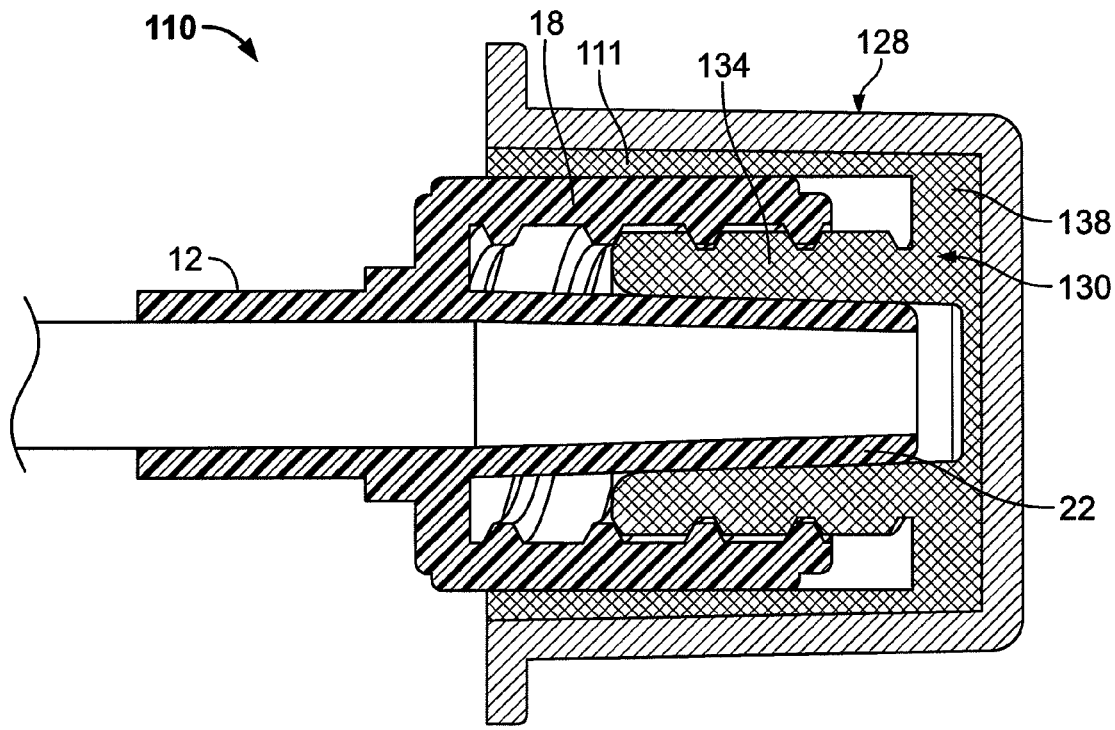
FIG. 5 is a cross-sectional view showing another embodiment of the antiseptic cap assembly, wherein a cap has an outer wall.

FIG. 5 shows another embodiment of an antiseptic cap assembly, indicated generally as 110, that is sized to engage and disinfect the male luer 22. The antiseptic cap assembly 110 operates and is constructed in manners consistent with the antiseptic cap assembly 10 shown in FIGS. 1-4, unless stated otherwise. Like the antiseptic cap assembly 10, the antiseptic cap assembly 110 includes a cap holder 128 and a cap 130 sized to be positioned within the cap holder 128.

In this embodiment, the cap 130 includes an annular sidewall 111 extending from an outer flange 138 and substantially concentric with the threaded portion 134. When the cap holder 128 is used, the annular sidewall 111 is positioned proximate an inner surface of the cap holder 12. When the antiseptic cap assembly 110 is attached to the luer connector 12, the annular sidewall 111 bears against the outer surface of the threaded portion 18 of the luer connector 12. The annular sidewall 111 can be made from porous plastic like the remainder of the cap 130 or any other suitable material. The annular sidewall 111 covers and protects the outer surface of the threaded portion 18 of the luer connector 12. The annular sidewall 111 may contain antiseptic fluid and release at least a portion of an antiseptic fluid.

Figure 6:
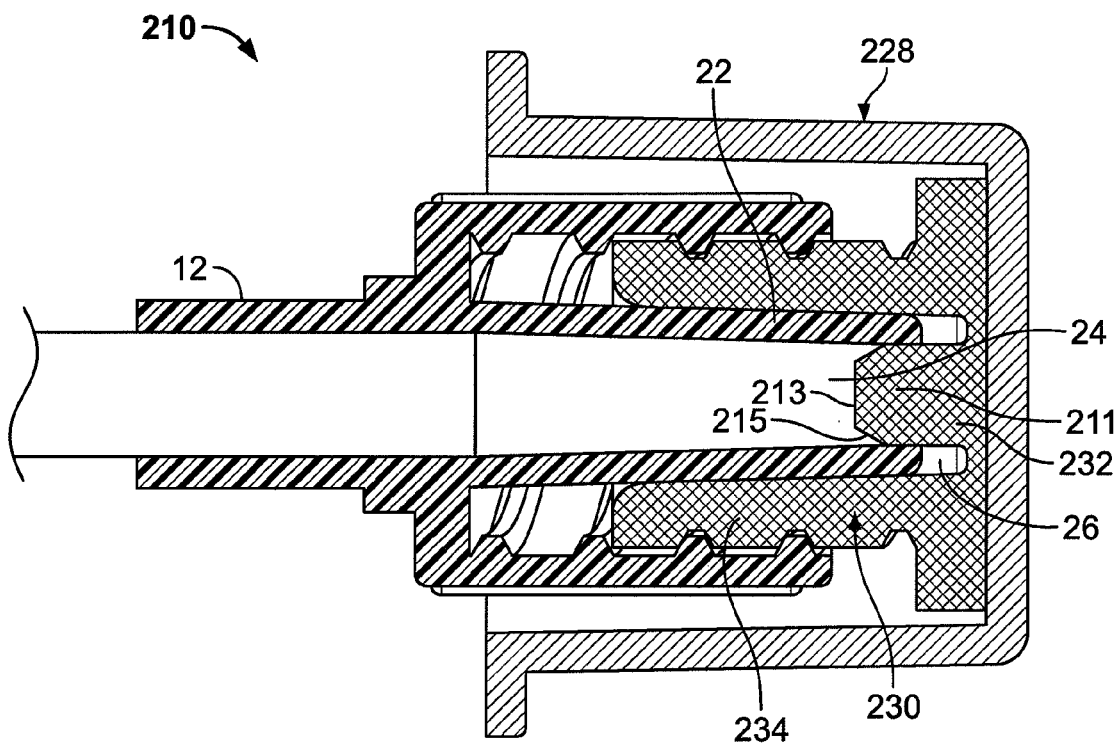
FIG. 6 is a cross-sectional view showing another embodiment of the antiseptic cap assembly, wherein the cap includes a center insert.

FIG. 6 shows another embodiment of an antiseptic cap assembly, indicated generally as 210, that is sized to engage and disinfect a male luer 22. The antiseptic cap assembly 210 operates and is constructed in manners consistent with the antiseptic cap assembly 10 shown in FIGS. 1-4, unless stated otherwise. Like the antiseptic cap assembly 10, the antiseptic cap assembly 210 includes a cap holder 228 and a cap 230 sized to be positioned within the cap holder 228.

In this embodiment, the cap 230 includes a center insert 211 that is integrally connected therewith. Alternatively, the cap 230 and the center insert 211 could be separate components. The center insert 211 may be made from porous plastic like the remainder of the cap 230 or any other suitable material, and may contain antiseptic fluid and release at least a portion of an antiseptic fluid. The center insert 211 could be treated with a hydrophilic surfactant, or otherwise made hydrophilic.

The center insert 211 protrudes from a base 232 of the cap 230 and is positioned within a threaded portion 234 of the cap 230. The center insert 211 has a distal end 213 that may have angled edges 215, thereby giving the center insert 211 a generally trapezoidal shape. The center insert 211 could define other shapes such as conical, square, rectangle, etc.

When the cap 230 is attached to a luer connector 12, the center insert 211 is positioned within the opening 24 formed in the male luer 22 and allows the antiseptic fluid to enter the male luer 22 to apply the antiseptic fluid to the inner tip 26 of the male luer 22.

Figure 7:
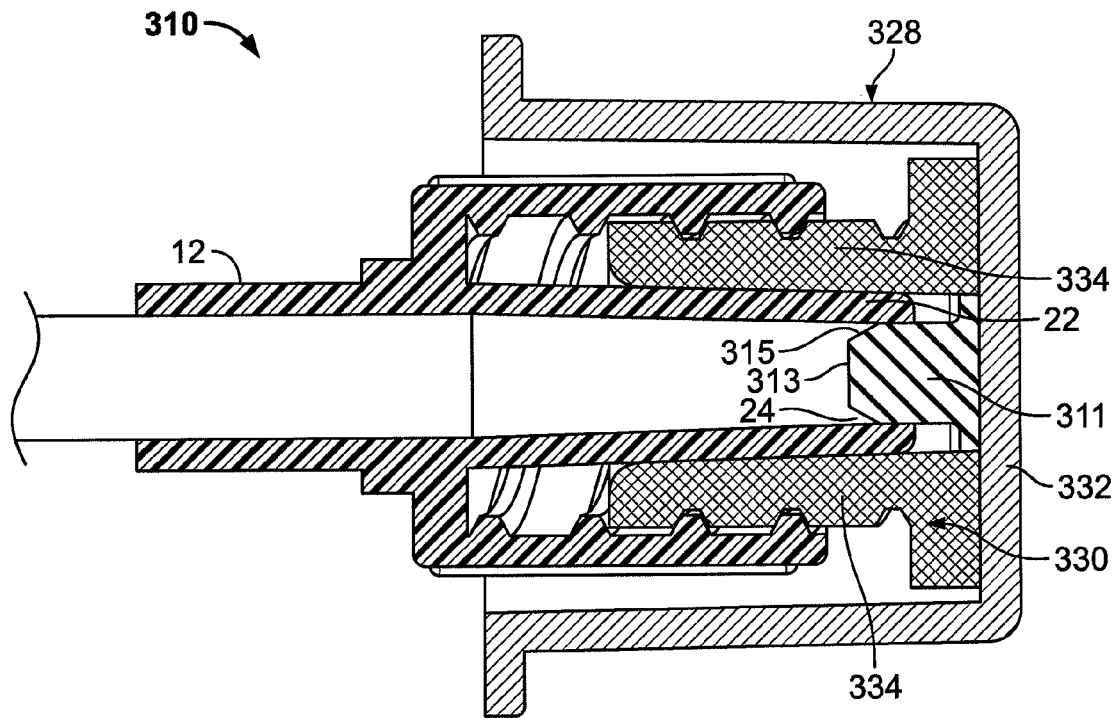
FIG. 7 is a cross-sectional view showing another embodiment of the antiseptic cap assembly, wherein the cap includes a center plug.

FIG. 7 shows another embodiment of an antiseptic cap assembly, indicated generally as 310, that is sized to engage and disinfect a male luer 22. The antiseptic cap assembly 310 operates and is constructed in manners consistent with the antiseptic cap assembly 10 shown in FIGS. 1-3, unless stated otherwise. Like the antiseptic cap assembly 10, the antiseptic cap assembly 310 includes a cap holder 328 and a cap 330 sized to be positioned within the cap holder 328.

In this embodiment, a sealing mechanism, such as a center plug 311, is sized to extend from a base 332 of the cap 330 and is sized to be positioned within the threaded portion 334 of the cap 330. The cap 330 and the center plug 311 could be separate components as shown or, alternatively, the cap 330 and the center plug 311 could be integrally formed. Alternatively, the center plug 311 could be an extension of the cap holder 328 molded in.

The center plug 311 has a distal end 313 that may have angled edges 315, thereby giving the center plug 311 a generally trapezoidal shape. The center plug 311 could define other shapes such as conical, square, rectangle, etc.

The center plug 311 bears against the opening 24 formed in the male luer 22 to prevent the antiseptic fluid from entering the male luer 22. The center plug 311 extends a distance from the base 332 sufficient to engage the opening 24 in the male luer 22 before the threaded portion 334 of the cap 330 is compressed by the male luer 22, to seal the opening 24 in the male luer 22.

The center plug 311 could be made of a non-porous material, such as rubber, or any other suitable material. The center plug 311 could be made of porous plastic and left in a hydrophobic state, i.e., not treated with a surfactant like the threaded portion 334 of the cap 330, thereby inhibiting or minimizing antiseptic fluid from passing therethrough and into the opening 24 formed in the male luer 22. In this manner, the center plug 311 serves to limit or prevent alcohol from entering the fluid line 316 of the luer connector 312. Also the center plug 311 could act as a plug to prevent IV fluid from dripping out of the line.

The configuration of the sealing mechanism is only exemplary. It will be understood that the present invention could employ other sealing mechanisms. For example, the sealing mechanism could be a center pin (not shown) sized to extend further into the opening 24 formed in the male luer 22 than the center plug 311. The center plug 311 may extend past the threads on the threaded portion 324 and inserted prior to thread engagement.

Figure 8:
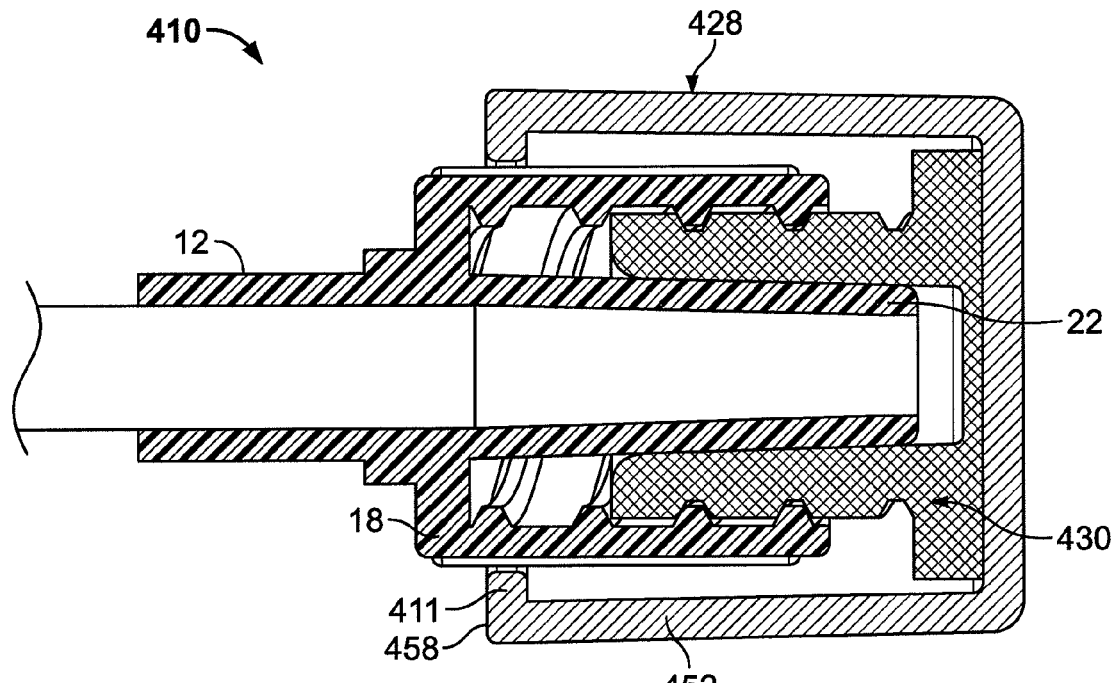
FIG. 8 is a cross-sectional view showing another embodiment of the antiseptic cap assembly, wherein a cap holder includes an inner-facing flange.

FIG. 8 shows another embodiment of an antiseptic cap assembly, indicated generally as 410, that is sized to engage and disinfect a male luer 22. The antiseptic cap assembly 410 operates and is constructed in manners consistent with the antiseptic cap assembly 10 shown in FIGS. 1-4, unless stated otherwise. Like the antiseptic cap assembly 10, the antiseptic cap assembly 410 includes a cap holder 428 and a cap 430 sized to be positioned within the cap holder 428.

In this embodiment, the cap holder 428 includes an inner-facing flange 411 that may form a protective seal that closes off the interior of the cap holder 428 when the antiseptic cap assembly 410 is engaged to the luer connector 12. The inner flange 411 extends radially inward from a distal end 458 of the sidewall 452 of the cap holder 428. When the antiseptic cap assembly 410 is engaged to the luer connector 12, the inner-facing flange 411 of the cap holder 428 may contact the threaded portion 18 of the luer connector 12 to seal the interior of the cap holder 428.

The inner-facing flange 411 of the cap holder 428 may provide a physical barrier to the ingress of pathogens, dust or other contaminants into the cap holder 428. The inner-facing flange 411 may serve to retain at least a portion of the antiseptic fluid from the antiseptic cap assembly 410 from leaking out. The inner-facing flange 411 may prevent evaporation of at least a portion of the antiseptic fluid that is retained.

The configuration of the cap holder 428 could vary. For example, the cap holder 428 could include an outer flange (not shown), such as the outer flange 56 (FIG. 1) that protrudes radially outwardly from the distal end 458 of the sidewall 452, as well as the inner-facing flange 411 that protrudes radially inward from the distal end 458 of the sidewall 452.

Figure 9:
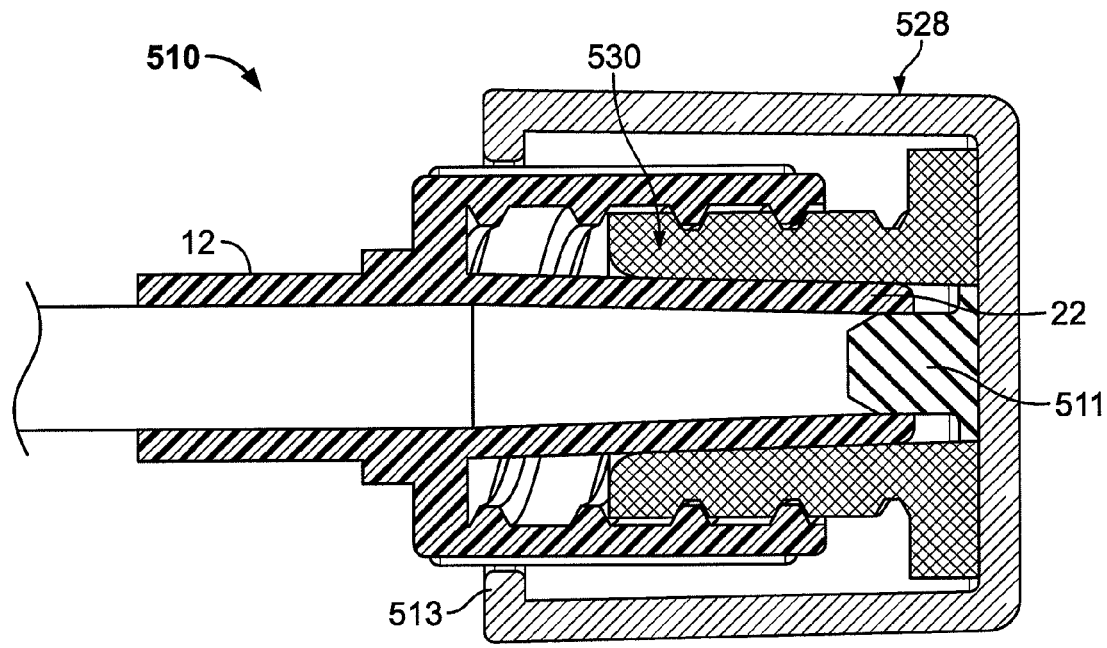
FIG. 9 is a cross-sectional view showing another embodiment of the antiseptic cap assembly, wherein a center plug is provided and the cap holder includes an inner-facing flange.

FIG. 9 shows another embodiment of an antiseptic cap assembly, indicated generally as 510, that is sized to engage and disinfect a male luer 22. The antiseptic cap assembly 510 operates and is constructed in manners consistent with the antiseptic cap assembly 10 shown in FIGS. 1-4, unless stated otherwise. Like the antiseptic cap assembly 10, the antiseptic cap assembly 510 includes a cap holder 528 and a cap 530 sized to be positioned within the cap holder 528.

In this embodiment, the antiseptic cap assembly 510 includes a center plug 511, such as the center plug 311 shown in FIG. 7. In addition, the cap holder includes an inner-facing flange 513, such as the flange 411 shown in FIG. 8.

It should be understood that various features of various embodiments disclosed herein could be used together without departing from the spirit or scope of the present invention.

Figure 10:
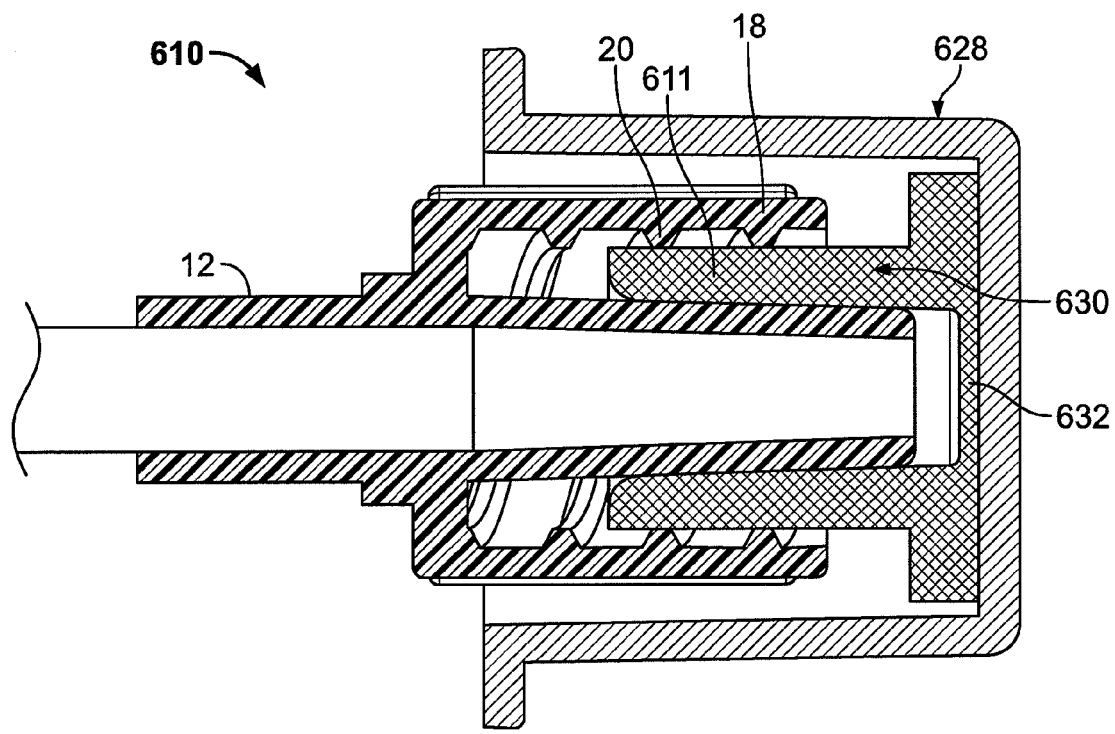
FIG. 10 is a cross-sectional view showing another embodiment of the antiseptic cap assembly, wherein a cap includes an annular portion without threads.

FIG. 10 shows another embodiment of an antiseptic cap assembly, indicated generally as 610, that is sized to engage and disinfect a male luer 22. The antiseptic cap assembly 610 operates and is constructed in manners consistent with the antiseptic cap assembly 10 shown in FIGS. 1-4, unless stated otherwise. Like the antiseptic cap assembly 10, the antiseptic cap assembly 610 includes a cap holder 628 and a cap 630 sized to be positioned within the cap holder 628.

In this embodiment, the cap 630 includes an annular portion 611 extending from a base 632. The annular portion 611 is configured without threads but is sized to engage the luer connector 12 with a push-on friction fit. The antiseptic cap assembly 610 could be removed by pulling out of the luer connector 12.

The annular portion 611 of the cap 630 could be configured such that the inner surface contacts the male luer 22 and is compressed by the male luer 22 to release antiseptic fluid when the cap 630 is pushed on to the male luer 22. The outer surface of the annular portion 611 could also contact against the inner threads 18 of the threaded portion 18 of the male luer 22 and could also release antiseptic fluid on this side. Alternatively, the annular portion 611 could be configured to avoid contact with the threads 20 of the luer connector 12. The annular portion 611 does not need to be tapered as shown.

Figure 11:
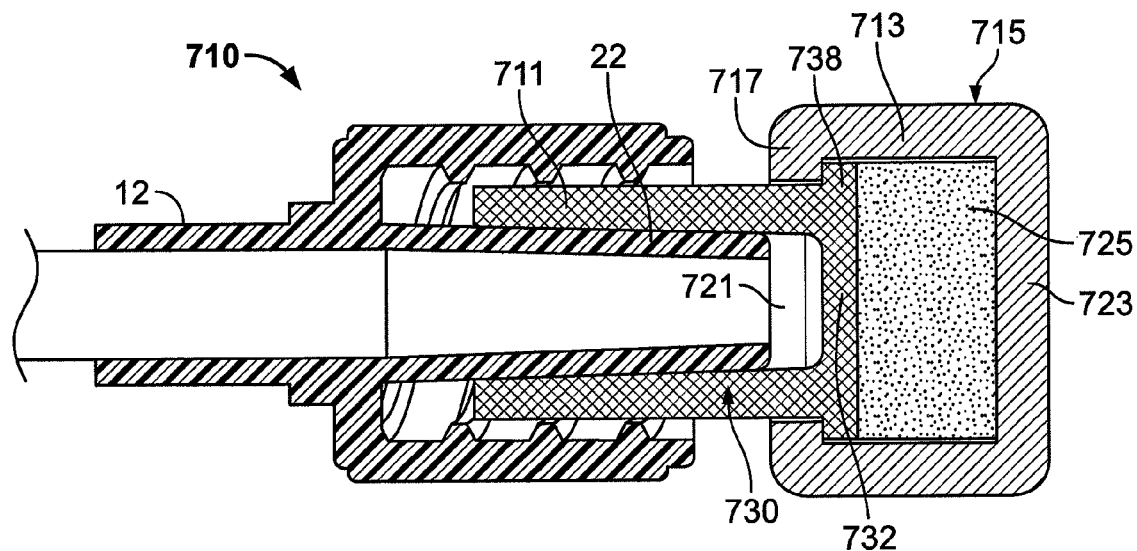
FIG. 11 is a cross-sectional view showing another embodiment of the antiseptic cap assembly, wherein an antiseptic cap assembly includes an antiseptic chamber.
Figure 12:
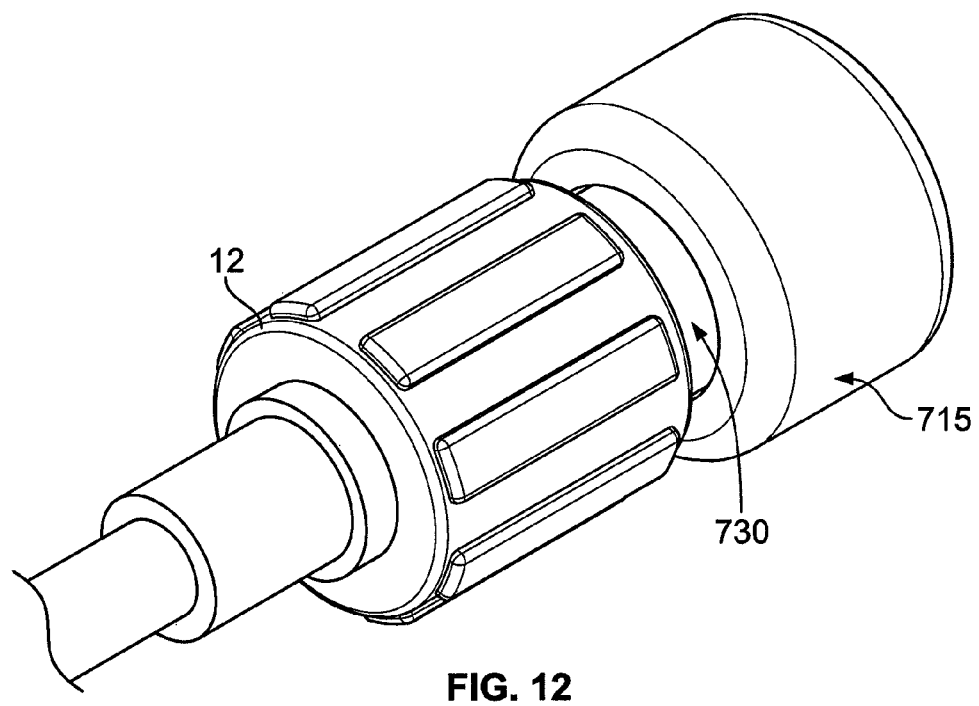
FIG. 12 is a perspective view of the antiseptic cap assembly shown in FIG. 11.

FIGS. 11 and 12 show another embodiment of an antiseptic cap assembly, indicated generally as 710, that is sized to engage and disinfect a male luer 22. The antiseptic cap assembly 710 operates and is constructed in manners consistent with the antiseptic cap assembly 10 shown in FIGS. 1-3, unless stated otherwise. The antiseptic cap assembly 710 includes an antiseptic chamber 715 and a cap 730.

In this embodiment, the cap 730 includes an annular portion 711 extending from a base 732. The annular portion 711 is configured and sized to engage the luer connector 12 with a push-on friction fit.

The antiseptic chamber 715 is attached to the base 732 of the cap 730 and is formed by a continuous sidewall 713 and an end wall 723. The sidewall 713 includes an inner flange 717 that extends radially inward from the sidewall 713. The flange 717 defines an open end 721.

The base 732 of the cap 730 is keyed to the antiseptic chamber 715. The base 732 of the cap 730 is positioned within the antiseptic chamber 715 such that the outer flange 738 of the base 732 is captured in the antiseptic chamber 715 by the inner flange 717 of the antiseptic chamber 715 which extends over the base 732. The base 732 closes off the disinfectant chamber 715 and the annular portion 711 of the cap 730 is in contact with the inner flange 717 of the antiseptic chamber 715. The cap 730 could be attached to the antiseptic chamber 715 such that the cap 730 rotates conjointly with the antiseptic chamber 715. In one embodiment, the base 732 of the cap 730 does not need to be keyed to the antiseptic chamber 715 in a push-on design.

The antiseptic chamber 715 can include an absorbent material 725, such as a pad, sponge, or elastomeric foam, configured to retain an antiseptic fluid. The absorbent material 725 could be wetted or soaked with the antiseptic fluid. The absorbent material 725 could be deformable. The cap 730 could be made from a porous plastic material that serves as a carrier for the transfer of antiseptic fluid from the disinfectant chamber 715. When the cap holder 728 is compressed, the absorbent material 725 releases at least a portion of the antiseptic fluid. The fluid can then flow through the base 732 and along the annular portion 711 to be delivered to the male luer 22. FIG. 12 shows a perspective view of the antiseptic cap assembly 710.

It will be understood that the present invention could employ other mechanisms that involve pushing on a component of an antiseptic cap assembly to activate or release the antiseptic fluid.

Figure 13:
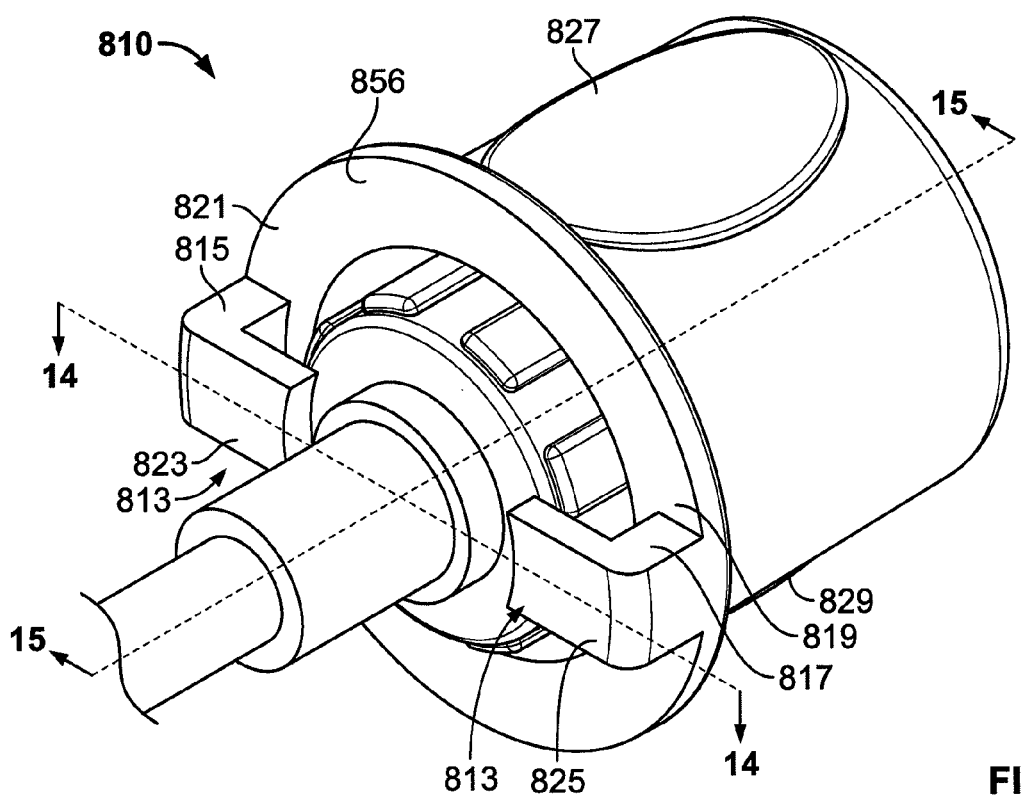
FIG. 13 is a perspective view showing another embodiment of the antiseptic cap assembly, wherein a cap holder includes retainers.
Figure 14:
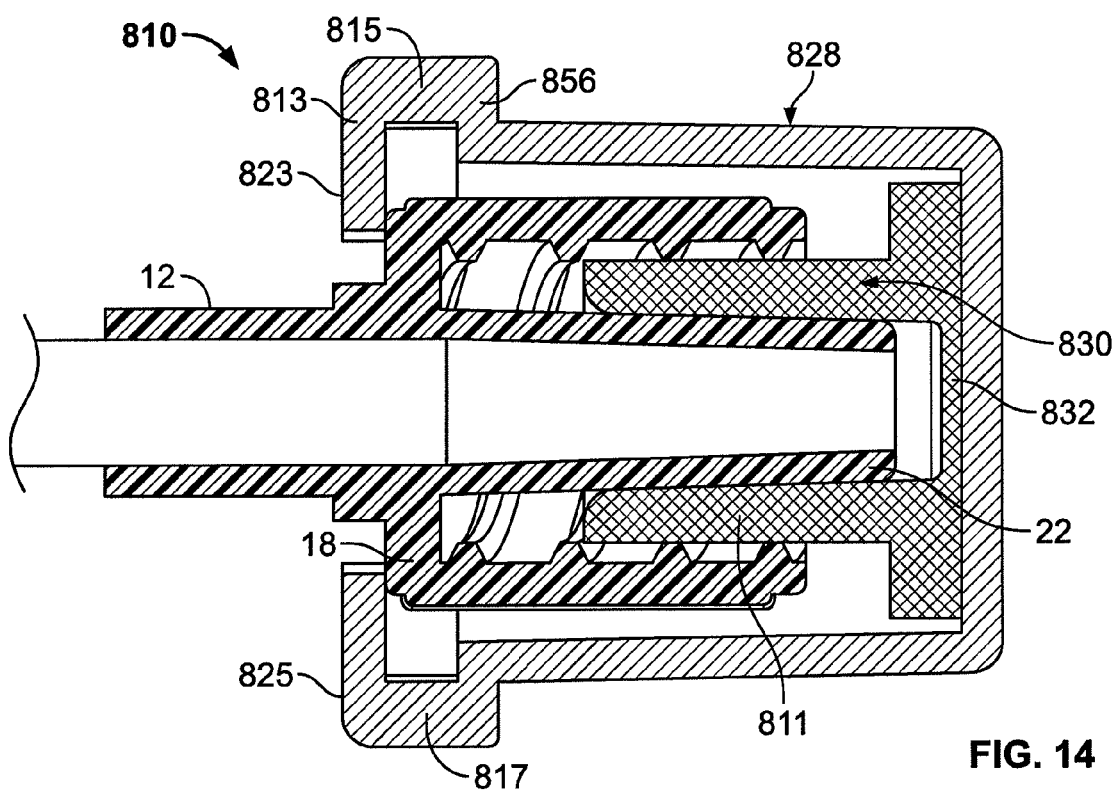
FIG. 14 is a cross-sectional view, taken along section lines 14-14 and looking in the direction of the arrows, of the antiseptic cap assembly shown in FIG. 13.
Figure 15:
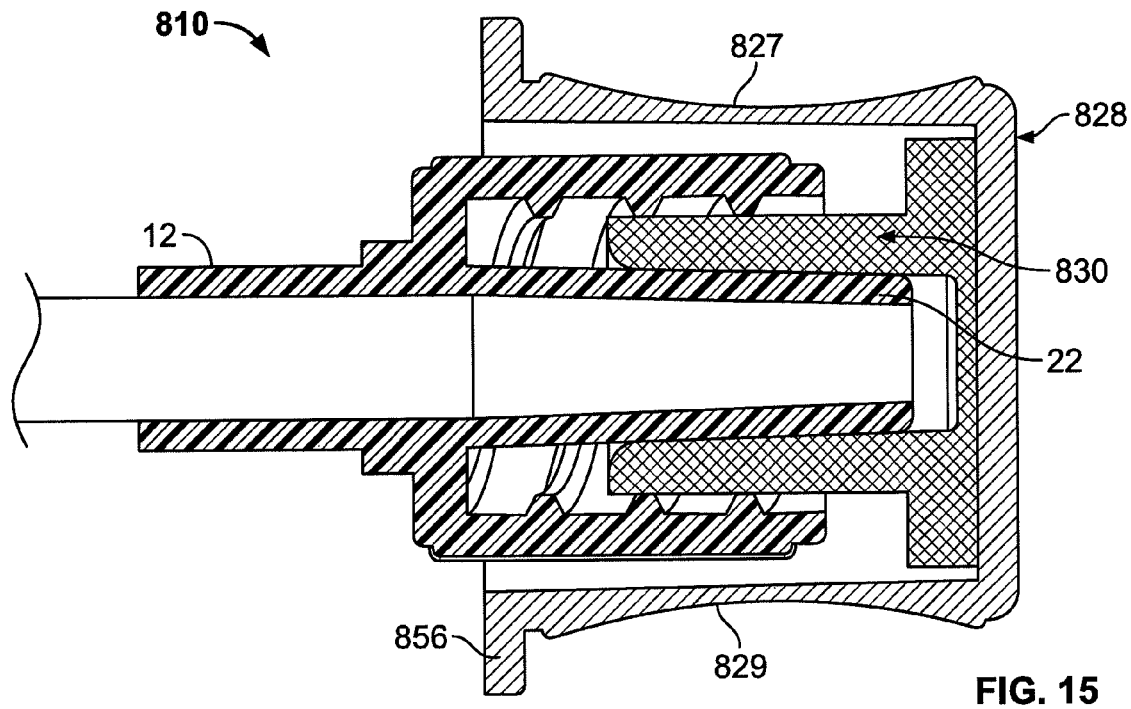
FIG. 15 is a cross-sectional view, taken along section lines 15-15, of the antiseptic cap assembly shown in FIG. 13.

FIGS. 13-15 show another embodiment of an antiseptic cap assembly, indicated generally as 810, that is sized to engage and disinfect a male luer 22. The antiseptic cap assembly 810 operates and is constructed in manners consistent with the antiseptic cap assembly 10 shown in FIGS. 1-3, unless stated otherwise. Like the antiseptic cap assembly 10, the antiseptic cap assembly 810 includes a cap holder 828 and a cap 830 sized to be positioned within the cap holder 828.

In this embodiment, the cap 830 includes an annular portion 811 extending from a base 832. The annular portion 811 is configured without threads and sized to engage the luer connector 12 with a push-on friction fit. The antiseptic cap assembly 810 could be removed by pulling out of the luer connector 12.

The cap holder 828 includes retainers 813 that serve to retain or secure the cap 830 on the luer connector 12. The retainers 813 include a pair of shoulders 815, 817 that extend perpendicularly from opposite sides of the outer flange 856 of the cap holder 828 and a pair of arms 823, 825 that extend radially inward from the shoulders 815, 817.

When the antiseptic cap assembly 810 is engaged to the luer connector 12, the arms 823, 825 of the retainers 813 extend over the male luer 22 to retain the cap 830. The retainers 813 could be made from a thermoplastic elastomer, such as SANTOPRENE, or any other suitable material. The retainers 813 could be made from a flexible material.

The cap holder 828 may include gripping areas defined by a recessed portion 827 (FIGS. 13 and 15) and a recessed portion 829 (FIGS. 13 and 15) on opposite sides of the outer sidewall 852. The recessed portions 827, 829 are configured for gripping the cap 830 to attach the cap 830 to the male luer 22.

Figure 16:
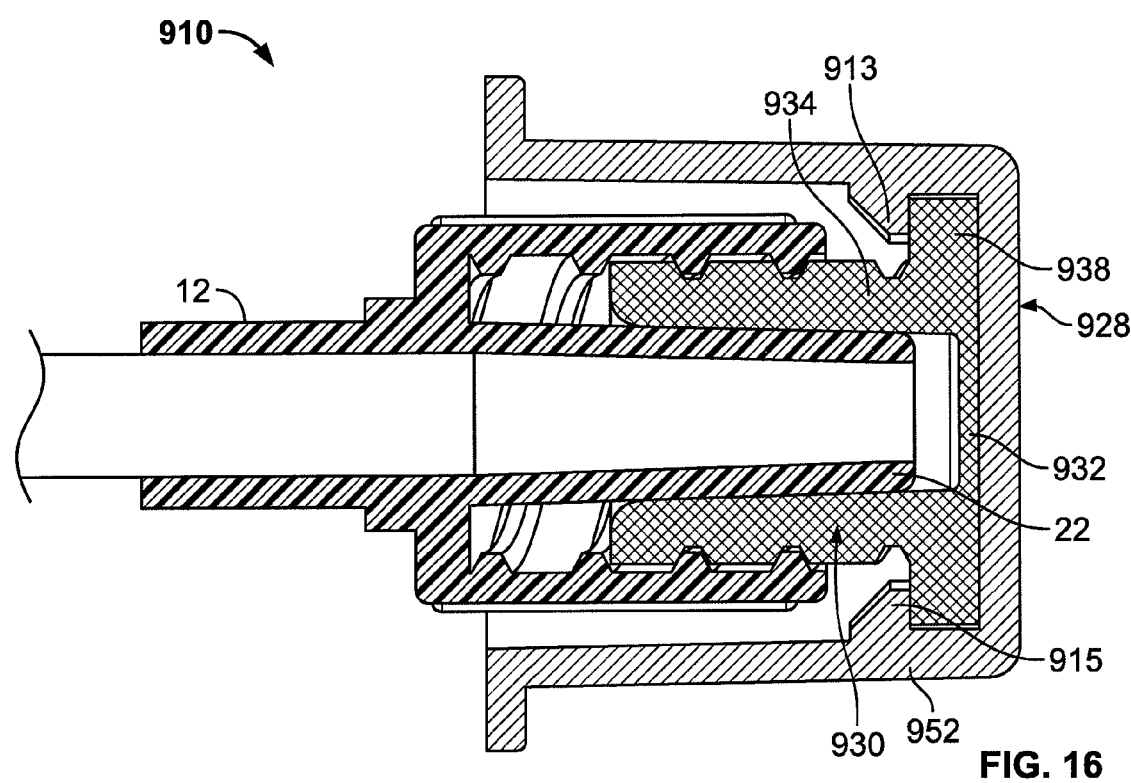
FIG. 16 is a cross-sectional view showing another embodiment of the antiseptic cap assembly, wherein an antiseptic cap assembly includes a ratchet assembly.
Figure 17:
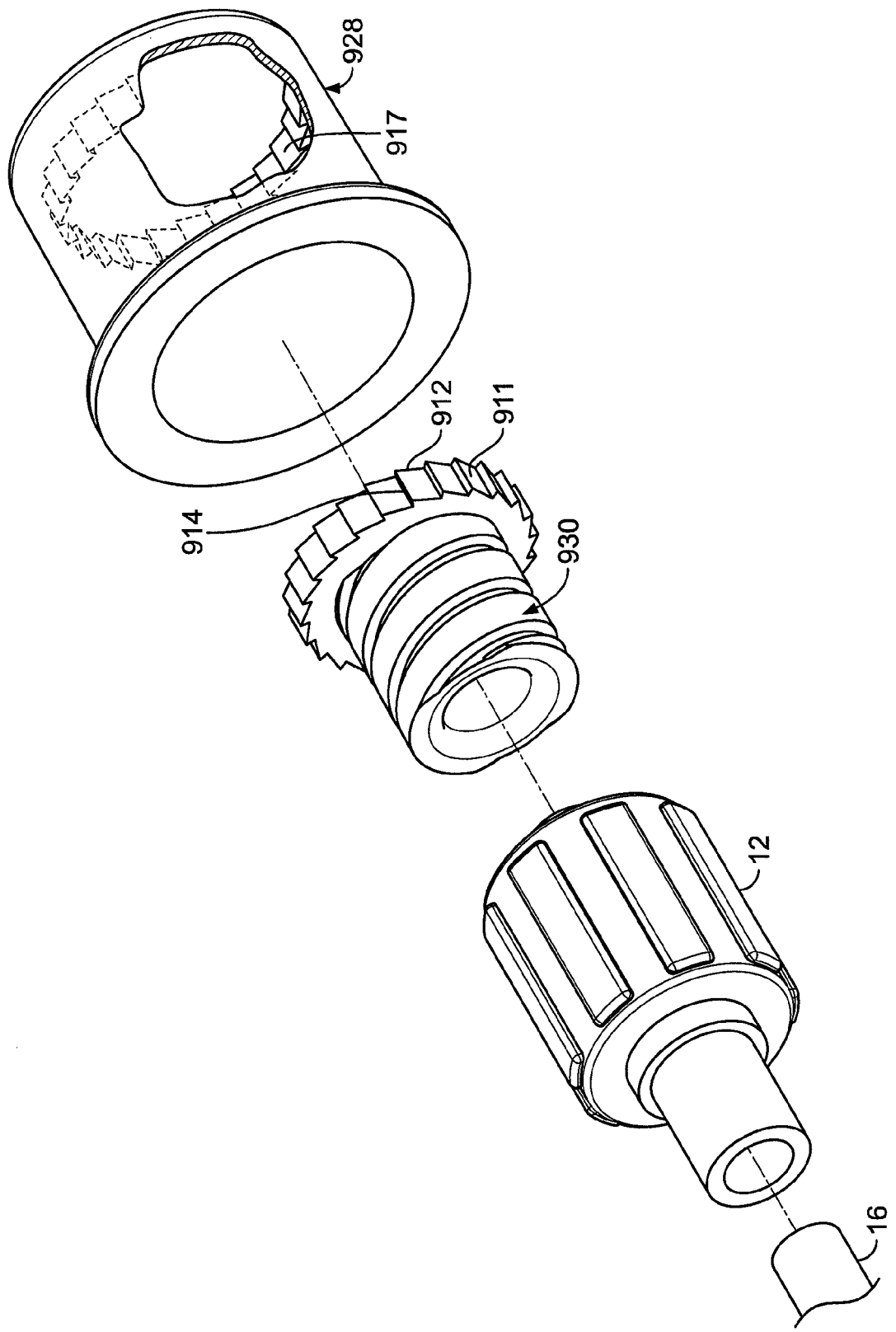
FIG. 17 is an exploded view of the antiseptic cap assembly shown in FIG. 16 and a luer connector.
Figure 18:
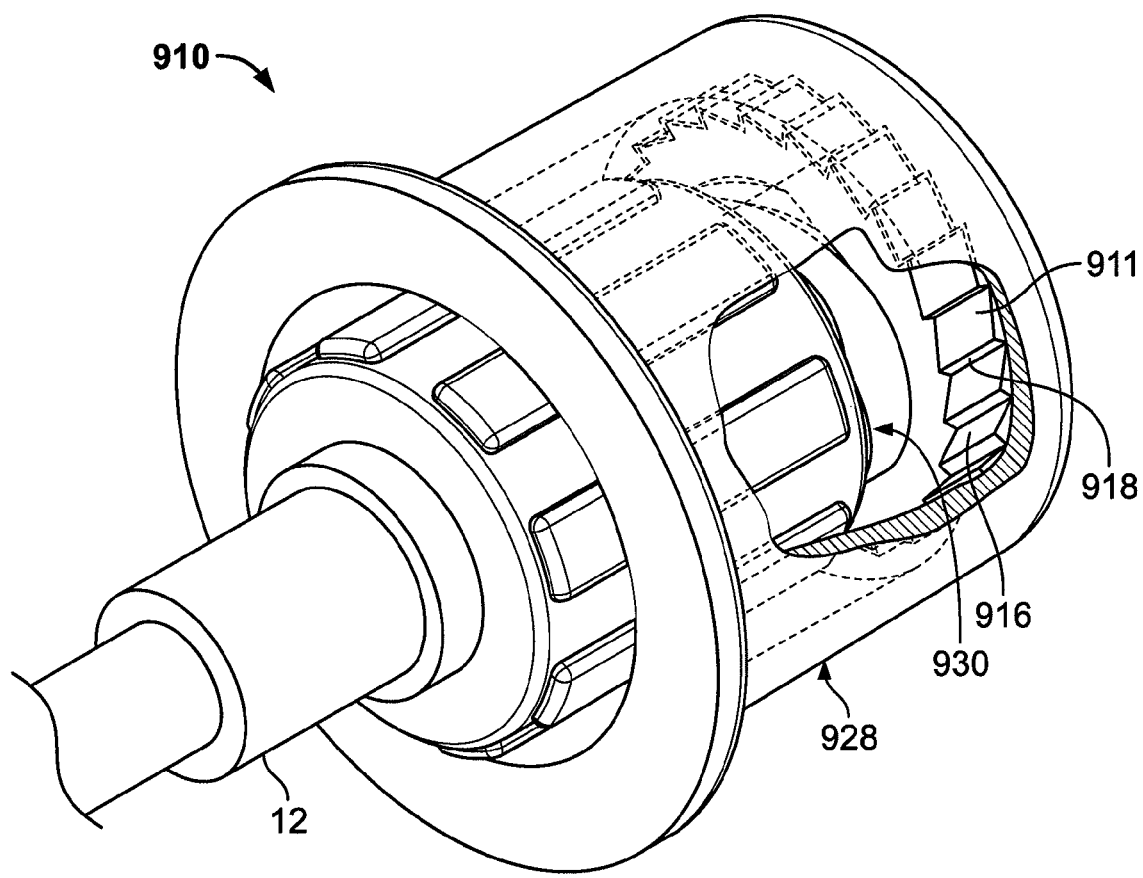
FIG. 18 is a partially cut away perspective view of an antiseptic cap assembly shown in FIG. 16 showing the ratchet assembly.

FIGS. 16-18 show another embodiment of an antiseptic cap assembly, indicated generally as 910, that is sized to engage and disinfect a male luer 22. The antiseptic cap assembly 910 operates and is constructed in manners consistent with the antiseptic cap assembly 10 shown in FIGS. 1-4, unless stated otherwise. Like the antiseptic cap assembly 10, the antiseptic cap assembly 910 includes a cap holder 928 and a cap 930 inserted within the cap holder 928. This embodiment includes a mechanism to prevent overtightening of the cap 930 on the male luer 22 which could damage the male luer 22. This is addressed with a ratchet assembly.

The cap 930 includes a base 932 and an annular threaded portion 934 extending from the base 932. The base 932 includes an outer flange 938 with a plurality of teeth 911 (see FIGS. 17 and 18), along the outer perimeter that allows for rotation in only one direction. Alternatively, it could be configured to allow for rotation in both directions by angling both surfaces of the teeth. The teeth 911 have angled faces 912 and generally perpendicular faces 914.

The cap holder 928 includes a retaining mechanism for retaining the cap 930 in the cap holder 928. The retaining mechanism could include a first protrusion 913 that extends from one section of the sidewall 952 of the cap holder 928, and a second protrusion 915 that extends from an opposite section of the sidewall 952 of the cap holder 928. The first and second protrusions 913, 915 are configured to extend over the base 932 of the cap 930. Alternatively, the retaining mechanism could include a single ring around the interior of the cap holder 928.

The cap holder 928 includes a plurality of teeth 917 that mate with the teeth 911 to form a ratchet mechanism. The teeth 917 interact with the teeth 911 to allow the cap 930 to rotate in the cap holder 928 in only one direction, and have angled faces 916 and generally perpendicular faces 918, like the teeth 911 of the base 932. Alternatively, it could be configured to allow for rotation in both directions.

The ratchet mechanism provides an audible or a tactile feedback to indicate that the antiseptic cap assembly 910 is properly secured. Also, the ratchet mechanism could limit torque to prevent damage to the luer connector 12 or to the cap 930. The cap 930 is threaded on the male luer 22 in accordance with other embodiments of the cap 930. If the cap 930 is turned beyond the limit of the threads, instead of damaging the male luer 22, the cap 930 will slide with respect to the cap holder 928, the angled teeth 911, 917 of the base 932 of the cap 930 and the cap holder 930 respectively sliding past one another to prevent further tightening of the cap 930 onto the male luer 22. When removing the cap 930 from the male luer 22, the generally perpendicular faces 914, 918 engage and do not permit sliding.

Figure 19:
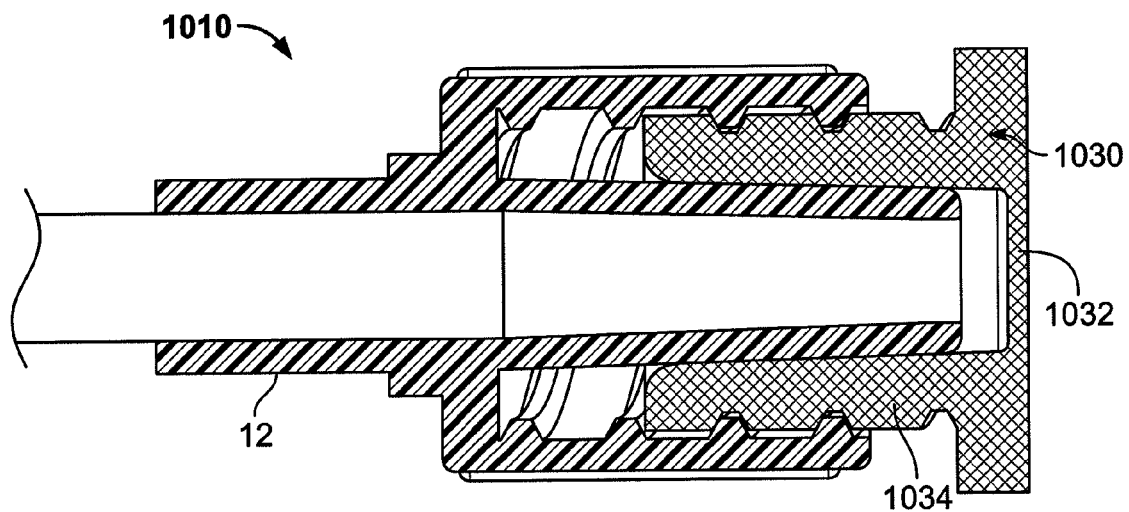
FIG. 19 is a perspective view showing an antiseptic cap assembly without a cap holder.

FIG. 19 shows another embodiment of an antiseptic cap assembly, indicated generally as 1010, that is sized to engage and disinfect a male luer 22. The antiseptic cap assembly 1010 operates and is constructed in manners consistent with the antiseptic cap assembly 10 shown in FIGS. 1-4, unless stated otherwise.

In this embodiment, the cap 1030 is used without a cap holder. The cap 1030 includes a base 1032 and an annular threaded portion 1034 extending from the base 1032. Antiseptic fluid can be associated with the interior surface of the annular threaded portion 1034.

The configuration of the cap 1030 is only exemplary. For example, the cap 1030 could be configured without threads and sized to engage the luer connector 12 with a push-on friction fit. Likewise, the cap 1030 could also include a sidewall, like that shown in FIG. 5.

Figure 20:
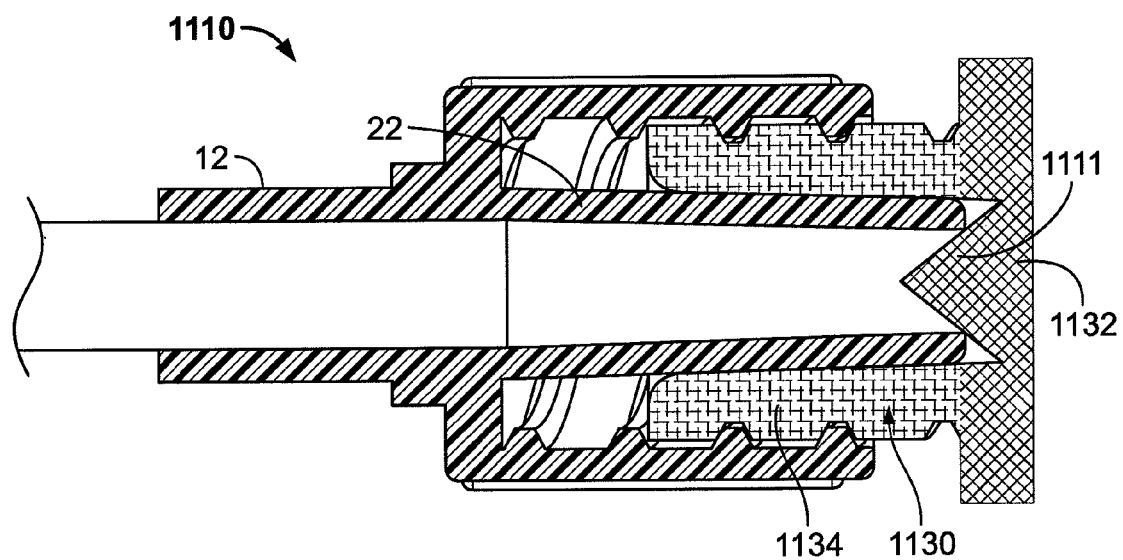
FIG. 20 is a cross-sectional view showing another embodiment of the antiseptic cap assembly of FIG. 19 having hydrophobic and hydrophilic sections.

FIG. 20 shows another embodiment of an antiseptic cap assembly, indicated generally as 1110, that is sized to engage and disinfect a male luer. The antiseptic cap assembly 1110 operates and is constructed in manners consistent with the antiseptic cap assembly 1010 shown in FIG. 18, unless stated otherwise.

In this embodiment, at least a portion of the cap 1130 could be treated with a hydrophilic surfactant, or otherwise made hydrophilic. In one embodiment, the threaded portion 1134 could be treated with a hydrophilic surfactant whereas the base 1132 could remain hydrophobic, so as to be resistant to and non-absorbent of an antiseptic fluid.

A center plug 1111 could bear against the opening 24 formed in the male luer 22 to prevent the antiseptic fluid from entering the male luer 22. The center plug 1111 could be made of porous plastic and left in a hydrophobic state, thereby inhibiting or minimizing antiseptic fluid from passing therethrough and into the opening 24 formed in the male luer 22. The hydrophobic section could also act as a plug in the IV line to preventingress of antiseptic fluid or to stop leakage of IV fluid.

Figure 21:
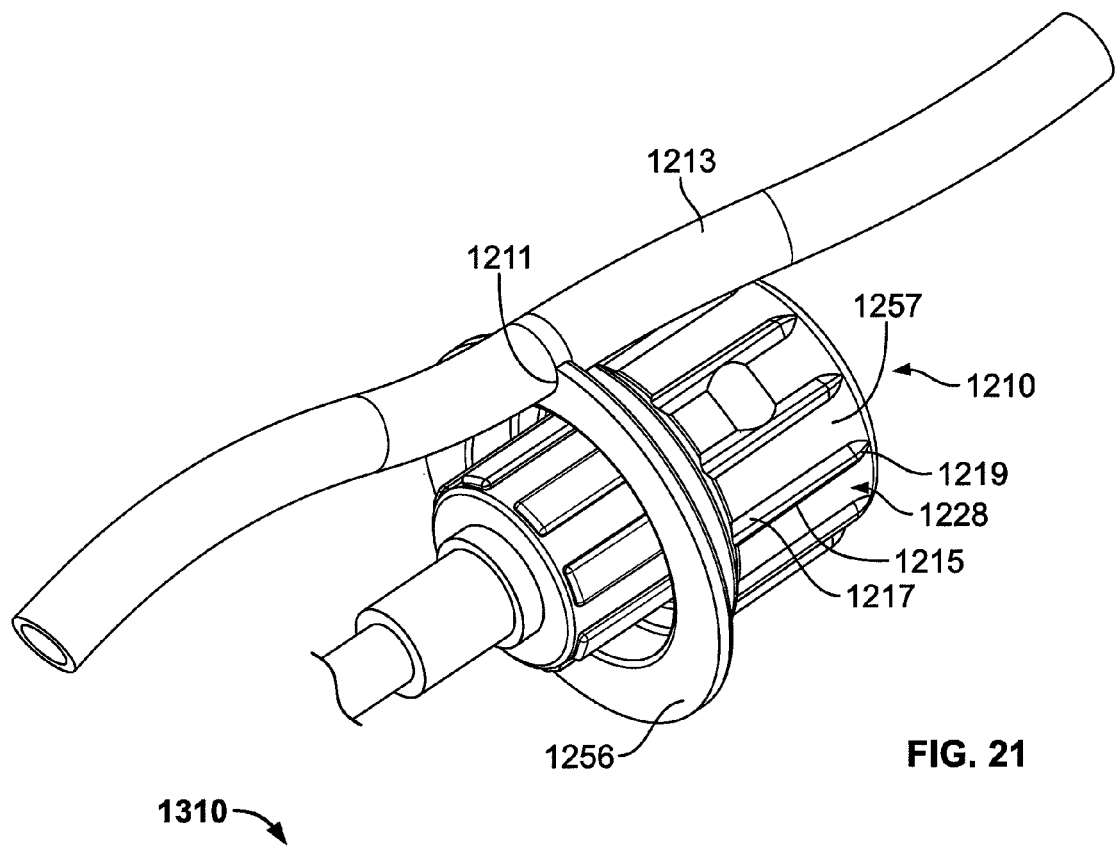
FIG. 21 is a perspective view showing another embodiment of the antiseptic cap assembly, wherein a cap holder has a flange with a recess for receiving a line.

FIG. 21 shows another embodiment of an antiseptic cap assembly, indicated generally as 1210, that is sized to engage and disinfect a male luer 22. The antiseptic cap assembly 1210 operates and is constructed in manners consistent with the antiseptic cap assembly 10 shown in FIGS. 1-4, unless stated otherwise.

The cap holder 1228 has a notch 1211 in an outer flange 1256 that is configured to attached to a supporting surface, such as a fluid line 1213. As shown, the cap holder 1228 has a plurality of ribs 1215 extending along a sidewall 1252 from one end 1217 of the cap holder 1228 to the opposite end 1219 of the cap holder 1228. The ribs 1215 facilitate gripping of the cap holder 1228.

Figure 22:
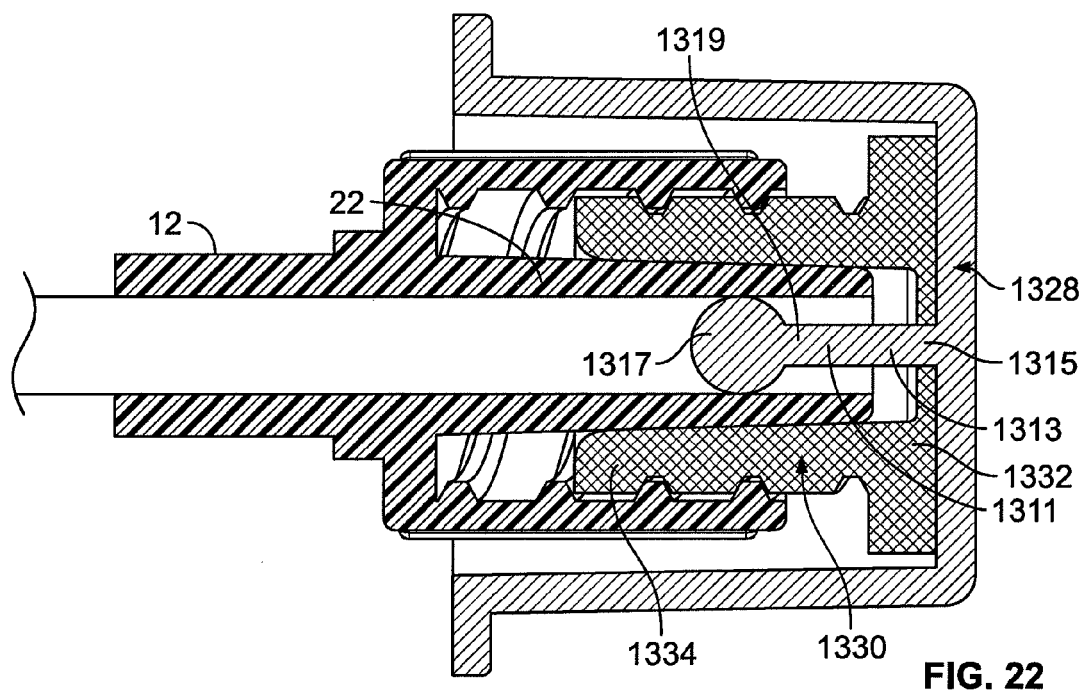
FIG. 22 is a cross-sectional view showing another embodiment of the antiseptic cap assembly, wherein a plug is supported by an arm.

FIG. 22 shows another embodiment of an antiseptic cap assembly, indicated generally as 1310, that is sized to engage and disinfect a male luer. The antiseptic cap assembly 1310 operates and is constructed in manners consistent with the antiseptic cap assembly 10 shown in FIGS. 1-3, unless stated otherwise. Like the antiseptic cap assembly 10, the antiseptic cap assembly 1310 includes a cap holder 1328 and a cap 1330 sized to be positioned within the cap holder 1328.

In this embodiment, a sealing mechanism, such as a center plug 1311, is sized to extend from the cap holder 1328 through the base 1332 and is sized to be positioned within the threaded portion 1334 of the cap 1330. As such, the center plug 1311 is made of a non-porous material such as SANTOPRENE, or any other suitable material. In particular, the center plug 1311 includes an arm 1313 with one end 1315 extending from the base 1332, and a sphere 1317 attached to an opposite end 1319 of the arm 1313. The sphere 1317 is configured to bear against the opening 24 formed in the male luer 22 to limit the distance that the antiseptic fluid can travel into the male luer 22. Alternatively, the center plug 1311 could extend from the base 1332 and be made of another material such as rubber. The sphere 1317 could be replaced with a non-spherical device.

Figure 23:
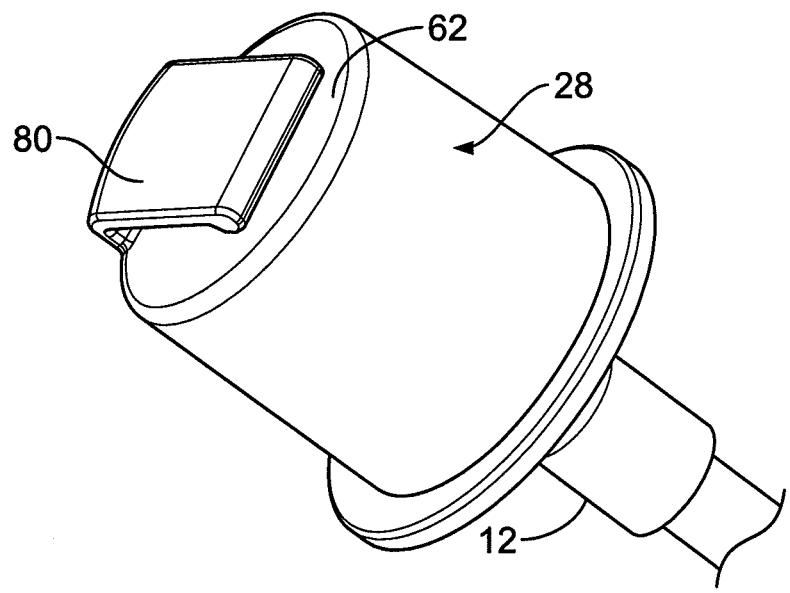
FIGS. 23-27 are perspective views showing an antiseptic cap assembly with various fastening mechanisms.
Figure 24:
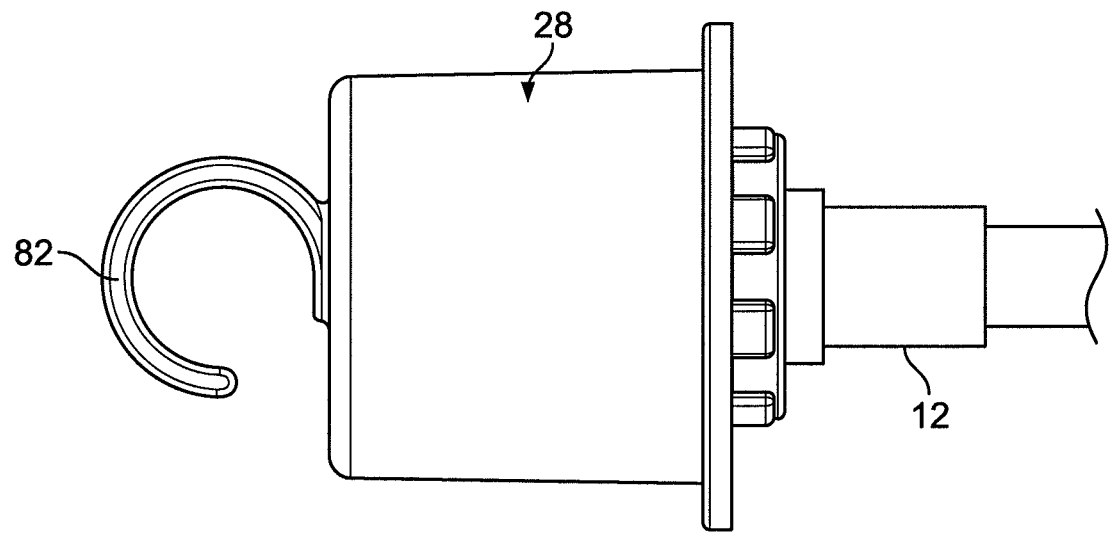

Any of the antiseptic cap assemblies 10, 110, 210, 310, 410, 510, 610, 710, 810, 910, 1010, 1110, 1210, and 1310 disclosed herein could be configured to be removably attached to a suitable surface (not shown), such as a IV bag, IV pump, or IV pole, etc., for use. For example, in FIG. 23, the substantially flat surface 62 of the cap holder 28 includes a clip 80 sized to removeably secure the antiseptic cap assembly 10 to a supporting surface (not shown), such as a IV bag. In FIG. 24, a hook 82 could be provided extending from the substantially flat surface 62 of the cap holder 28 and sized to removeably secure the antiseptic cap assembly 10 to a supporting surface (not shown).

Figure 25:
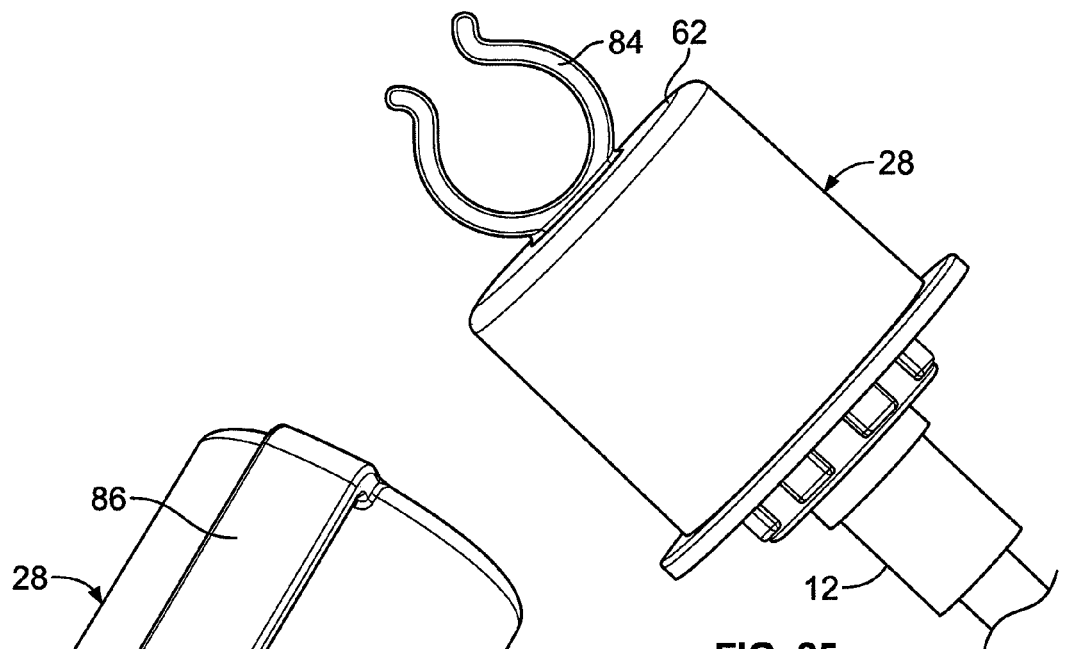
Figure 26:
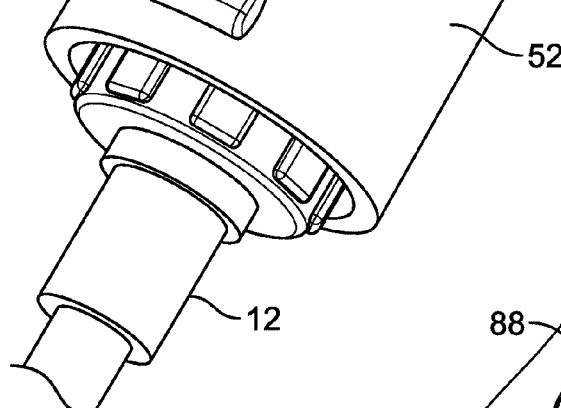

In FIG. 25, a horseshoe-shaped clip 84 could be provided extending from the substantially flat surface 62 of the cap holder 28 and sized to releasably fasten an antiseptic cap assembly 10 to a supporting surface (not shown). The location of a fastening member could vary. For example, in FIG. 26, the sidewall 52 of the cap holder 28 includes a clip 86.

Figure 27:
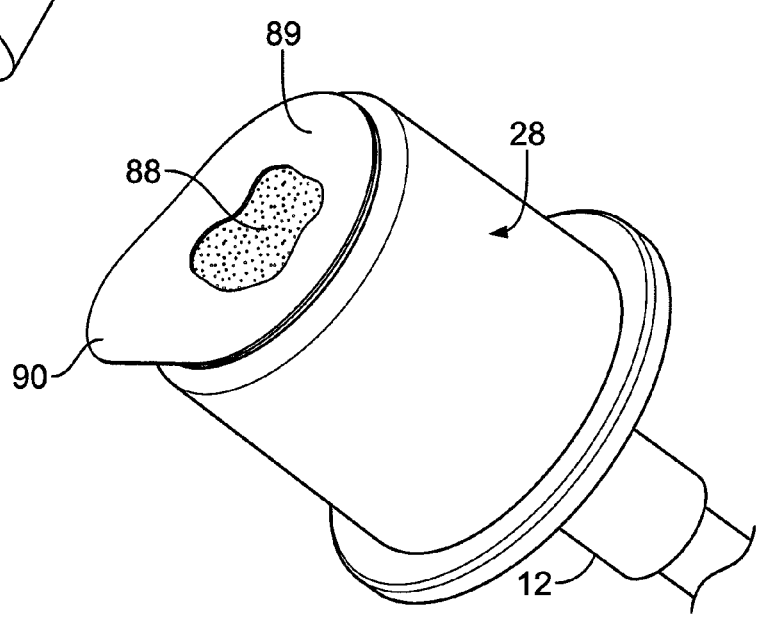

In FIG. 27, the end surface 62 of the cap holder 28 includes an adhesive 88 that could be covered by a release sheet 89. The adhesive 88 could be used to attach the antiseptic cap assembly 10 to a supporting surface, such as a IV pole. A pull tab 90 could be provided to remove the release sheet 89 to expose the adhesive 88.

Alternative fastening mechanisms could be provided. For example, the antiseptic cap assembly could include a ring (not shown).

The antiseptic cap assembly could be incorporated in kits with flush syringes, caps for treating a catheter or needleless connector, and line access devices, etc. The antiseptic fluid used could include an anticoagulant material, and/or an antimicrobial material. Examples of antiseptic fluid that could be used are disclosed in U.S. patent application Ser. Nos. 11/821,190, filed on Jun. 22, 2007, and 12/214,526, filed on Jun. 19, 2008. The entire disclosures of U.S. patent application Ser. Nos. 11/821,190 and 12/214,526 are incorporated herein by reference in their entirety.

Antiseptic Coatings

It is contemplated that the devices described herein can be coated with an antiseptic coating by any suitable technique such as immersion of the part into an antiseptic solution, by spray coating the part with the antiseptic solution, by blending the antiseptic solution or material into the polymeric material used to fabricate the device.

A quantity of physiological, antimicrobial metal compound is added to the resin for direct molding of an article. Physiological, antimicrobial metals are meant to include the precious metals, such as silver, gold and platinum, and copper and zinc. Physiological, antimicrobial metal compounds used herein include oxides and salts of preferably silver and also gold, for example: silver acetate, silver benzoate, silver carbonate, silver citrate, silver chloride, silver iodide, silver nitrate, silver oxide, silver sulfa diazine, silver sulfate, gold chloride and gold oxide. Platinum compounds such as chloroplatinic acid or its salts (e.g., sodium and calcium chloroplatinate) may also be used. Also, compounds of copper and zinc may be used, for example: oxides and salts of copper and zinc such as those indicated above for silver. Single physiological, antimicrobial metal compounds or combinations of physiological, antimicrobial metal compounds may be used.

Preferred physiological, antimicrobial metal compounds used in this invention are silver acetate, silver oxide, silver sulfate, gold chloride and a combination of silver oxide and gold chloride. The particles of the silver compounds are sufficiently able to be extracted to form a zone of inhibition to prevent and kill bacteria growth.

In another preferred form of the invention the devices herein are impregnated with triclosan and silver compounds or triclosan and chlorhexidine, or chlorhexidine gluconate, or chlorhexidine acetate.

It will be understood that the embodiments described herein are merely exemplary and that a person skilled in the art may make many variations and modifications without departing from the spirit and scope of the invention. All such variations and modifications are intended to be included within the scope of the invention as defined by the appended claims.

What is claimed is:

1. An antiseptic cap for use with a male luer medical connector comprising a threaded portion of a male luer including engaging features on an inner surface thereof, the antiseptic cap comprising:

a cap having a base and an annular portion extending from the base, the base comprising an outer annular flange configured to extend radially beyond the threaded portion of the male luer medical connector when the cap is engaged with the male luer medical connector, the annular portion comprising an inner surface defining a chamber having an open end, a closed end, and an external surface, the external surface concentric with the inner surface, the cap being made of a substantially rigid, compressible and absorbent material, wherein the chamber is configured to receive a tip portion of the male luer; and an antiseptic fluid retained within the compressible and absorbent material, wherein the antiseptic fluid is configured to be released from the compressible and absorbent material upon compression of the external surface by engagement of the cap.

2. The antiseptic cap of claim 1, wherein the cap comprises sintered porous plastic material.

3. The antiseptic cap of claim 1, wherein the annular portion includes a rim defining the open end, the annular portion being tapered to narrow from the rim toward the base.

4. The antiseptic cap of claim 1, wherein the annular portion is hydrophilic, and the base is hydrophobic.

5. The antiseptic cap of claim 1, wherein the annular portion is integral with the base.

6. The antiseptic cap of claim 1, wherein the annular portion of the cap is made of a substantially rigid, compressible and absorbent material.

7. The antiseptic cap of claim 1, wherein the annular portion is integral with the base, and wherein the annular portion of the cap is made of a substantially rigid, compressible and absorbent material.

8. The antiseptic cap of claim 1, wherein the external surface includes external threads and wherein the antiseptic fluid is configured to be released from the compressible and absorbent material upon compression of the external surface by threaded engagement of the cap.

9. The antiseptic cap of claim 1, further comprising a cap holder, wherein the cap is removably attached to the cap holder.

10. An antiseptic cap for use with a male luer medical connector comprising a threaded portion of a male luer including engaging features on an inner surface thereof, the antiseptic cap comprising:

a cap having a base and an annular portion extending from the base, the base comprising an outer annular flange configured to extend radially beyond the threaded portion of the male luer medical connector when the cap is engaged with the male luer medical connector, the annular portion comprising an inner surface defining a first chamber having an open end and an external surface, the external surface concentric with the inner surface, the cap being made of a substantially rigid, compressible and absorbent material, wherein the annular portion is configured to extend between the male luer and the threaded portion;

a cap holder having a base surface and a sidewall defining a second chamber sized to receive the cap, the cap disposed within the second chamber; and an antiseptic agent retained within the compressible and absorbent material, wherein the antiseptic agent is configured to be released from the compressible and absorbent material upon compression of the external surface by engagement of the cap.

11. The antiseptic cap assembly of claim 10, wherein the cap comprises sintered porous plastic material.

12. The antiseptic cap assembly of claim 10, wherein the antiseptic agent comprises an antiseptic fluid.

13. The antiseptic cap assembly of claim 10, wherein the base of the cap includes a substantially flat surface.

14. The antiseptic cap of claim 10, wherein the annular portion is integral with the base.

15. The antiseptic cap of claim 10, wherein the annular portion of the cap is made of a substantially rigid, compressible and absorbent material.

16. The antiseptic cap of claim 10, wherein the annular portion is integral with the base, and wherein the annular portion of the cap is made of a substantially rigid, compressible and absorbent material.

17. The antiseptic cap assembly of claim 10, wherein the external surface includes external threads and wherein the antiseptic fluid is configured to be released from the compressible and absorbent material upon compression of the external surface by threaded engagement of the cap.

18. The antiseptic cap assembly of claim 10, wherein the cap is removably attached to the cap holder.

19. The antiseptic cap assembly of claim 10, wherein the sidewall is generally cylindrical.

20. An antiseptic cap for use with a male luer medical connector comprising a threaded portion of a male luer including engaging features on an inner surface thereof, the antiseptic cap comprising:
   a cap having a base and an annular portion extending from the base, the base comprising an outer annular flange configured to extend radially beyond the threaded portion of the male luer medical connector when the cap is engaged with the male luer medical connector, the annular portion comprising an inner surface defining a first chamber having an open end and an external surface, the external surface concentric with the inner surface, the cap being made of a substantially rigid, compressible and absorbent material, wherein the chamber is configured to receive a tip portion of the male luer;
   an antiseptic fluid retained within the compressible and absorbent material, wherein the antiseptic fluid is configured to be released from the compressible and absorbent material upon compression of the external surface by engagement of the cap; and
   a removable seal configured to limit evaporation of the fluid from the cap.

21. The antiseptic cap assembly of claim 20, further comprising a cap holder having a sidewall defining a second chamber sized to receive the cap.

22. The antiseptic cap assembly of claim 21, wherein the cap comprises sintered porous plastic material.

23. The antiseptic cap of claim 21, wherein the annular portion includes a rim defining the open end, the annular portion being tapered to narrow from the rim toward the base.

24. The antiseptic cap assembly of claim 21, wherein the cap is removably attached to the cap holder.

25. The antiseptic cap assembly of claim 21, wherein the sidewall is generally cylindrical.

26. The antiseptic cap assembly of claim 21, wherein the removable seal is attached to the cap holder to selectively seal the second chamber.

27. The antiseptic cap of claim 20, wherein the antiseptic fluid comprises an alcohol.

28. The antiseptic cap of claim 27, wherein the alcohol is isopropyl alcohol.

29. The antiseptic cap of claim 20, wherein the antiseptic fluid comprises chlorhexidine.

30. The antiseptic cap of claim 20, wherein the cap comprises sintered porous plastic material, bonded fiber, cotton, silicone, urethane, polyester, or cellulose.

31. The antiseptic cap of claim 30, wherein the sintered porous plastic material comprises a polymer.

32. The antiseptic cap of claim 31, wherein the polymer comprises polyethylene, polypropylene, or nylon.

33. The antiseptic cap of claim 20, wherein the annular portion is integral with the base.

34. The antiseptic cap of claim 20, wherein the annular portion of the cap is made of a substantially rigid, compressible and absorbent material.

35. The antiseptic cap of claim 20, wherein the annular portion is integral with the base, and wherein the annular portion of the cap is made of a substantially rigid, compressible and absorbent material.

36. The antiseptic cap assembly of claim 20, wherein the external surface includes external threads and wherein the antiseptic fluid is configured to be released from the compressible and absorbent material upon compression of the external surface by threaded engagement of the cap.

* * * * *

UNITED STATES PATENT AND TRADEMARK OFFICE
CERTIFICATE OF CORRECTION

| | | |
|---|---|---|
| PATENT NO. | : 9,867,975 B2 | Page 1 of 2 |
| APPLICATION NO. | : 13/113777 | |
| DATED | : January 16, 2018 | |
| INVENTOR(S) | : Christopher E. Gardner | |

It is certified that error appears in the above-identified patent and that said Letters Patent is hereby corrected as shown below:

On the Title Page

Item (56), References Cited, Column 2 above *cited by examiner, insert --Hospira, "You Work in Neverland," Lifeshield Product Brochure in 2 pages, Published 2009.--.

In the Specification

In Column 3 at Line 47, Change "Porex." to --Porex--.

In Column 10 at Line 8, Change "preventingress" to --prevent ingress--.

In Column 11 at Line 32, Change "sulfa diazine," to --sulfadiazine,--.

In the Claims

In Column 12 at Line 38, In Claim 10, change "antiseptic cap" to --antiseptic cap assembly--.

In Column 13 at Line 1, In Claim 14, change "antiseptic cap" to --antiseptic cap assembly--.

In Column 13 at Line 3, In Claim 15, change "antiseptic cap" to --antiseptic cap assembly--.

In Column 13 at Line 6, In Claim 16, change "antiseptic cap" to --antiseptic cap assembly--.

In Column 13 at Line 19, In Claim 20, change "antiseptic cap" to --antiseptic cap assembly--.

In Column 14 at Line 3, In Claim 23, change "antiseptic cap" to --antiseptic cap assembly--.

In Column 14 at Line 15, In Claim 27, change "antiseptic cap" to --antiseptic cap assembly--.

In Column 14 at Line 17, In Claim 28, change "antiseptic cap" to --antiseptic cap assembly--.

Signed and Sealed this
Twenty-second Day of May, 2018

Andrei Iancu
*Director of the United States Patent and Trademark Office*

CERTIFICATE OF CORRECTION (continued)
U.S. Pat. No. 9,867,975 B2

In Column 14 at Line 19, In Claim 29, change "antiseptic cap" to --antiseptic cap assembly--.

In Column 14 at Line 21, In Claim 30, change "antiseptic cap" to --antiseptic cap assembly--.

In Column 14 at Line 24, In Claim 31, change "antiseptic cap" to --antiseptic cap assembly--.

In Column 14 at Line 27, In Claim 32, change "antiseptic cap" to --antiseptic cap assembly--.

In Column 14 at Line 29, In Claim 33, change "antiseptic cap" to --antiseptic cap assembly--.

In Column 14 at Line 31, In Claim 34, change "antiseptic cap" to --antiseptic cap assembly--.

In Column 14 at Line 34, In Claim 35, change "antiseptic cap" to --antiseptic cap assembly--.